US010492977B2

United States Patent
Kapure et al.

(10) Patent No.: US 10,492,977 B2
(45) Date of Patent: Dec. 3, 2019

(54) APPARATUS AND SYSTEM FOR LIMB REHABILITATION

(71) Applicant: Bionic Yantra Private Limited, Bangalore (IN)

(72) Inventors: Kaustubh Kapure, Aurangabad (IN); Girish Mudgal, Ghaziabad (IN); Utsav Shah, Ahmedabad (IN); Kush Kumar Goyal, Alwar (IN); Sumit Dahiya, New Delhi (IN)

(73) Assignee: Bionic Yantra Private Limited, Bangalore (IN)

( * ) Notice: Subject to any disclaimer, the term of this patent is extended or adjusted under 35 U.S.C. 154(b) by 0 days.

(21) Appl. No.: 16/204,836

(22) Filed: Nov. 29, 2018

(65) Prior Publication Data

US 2019/0183715 A1    Jun. 20, 2019

(51) Int. Cl.
| | | |
|---|---|---|
| *A61H 3/00* | (2006.01) | |
| *G16H 20/30* | (2018.01) | |
| *A61H 1/02* | (2006.01) | |
| *G16H 50/20* | (2018.01) | |
| *A61H 3/04* | (2006.01) | |

(52) U.S. Cl.
CPC ........... *A61H 3/008* (2013.01); *A61H 1/0262* (2013.01); *G16H 20/30* (2018.01); *G16H 50/20* (2018.01); *A61H 2003/007* (2013.01); *A61H 2003/043* (2013.01); *A61H 2201/149* (2013.01); *A61H 2201/163* (2013.01); *A61H 2201/1642* (2013.01); *A61H 2201/1652* (2013.01); *A61H 2201/1659* (2013.01); *A61H 2201/5012* (2013.01); *A61H 2201/5058* (2013.01)

(58) Field of Classification Search
CPC ......... A61H 3/008; G16H 20/30; G16H 50/20
See application file for complete search history.

(56) References Cited

U.S. PATENT DOCUMENTS

| | | | | |
|---|---|---|---|---|
| 2005/0171410 A1* | 8/2005 | Hjelt | ........................ | A61B 5/00 600/300 |
| 2014/0058299 A1* | 2/2014 | Sankai | ................... | A61B 5/112 601/35 |
| 2014/0213951 A1* | 7/2014 | Pietrusisnki | ........... | A61H 1/024 602/23 |
| 2018/0071580 A1* | 3/2018 | Lee | .......................... | A61H 3/00 |

* cited by examiner

*Primary Examiner* — Yashita Sharma
(74) *Attorney, Agent, or Firm* — Greeta Kadambi; Riddhi IP LLC

(57) ABSTRACT

A robotic limb rehabilitation apparatus and system for a lower limb in a human being is disclosed. The apparatus comprises of a mobile-frame, dynamic weight unloading mechanism and lower extremity exoskeleton device. The mobile-frame structure is constructed using first and second vertical structural support members connected by a horizontal cross bar/beam to which a boom arm assembly is attached. During the rehabilitation exercises the user is secured with a harness and lower extremity exoskeleton device for safe movements. An intelligent algorithm, embedded onto a dedicated processor, actuates various motors to execute the prescribed exercises, while the sensors provide dynamic feedback for corrective measures to control the exercise routine.

7 Claims, 25 Drawing Sheets

Rosemary Vanguard | 38 yrs | Spinal Cord Injury | 3/10 sessions 30 sec "Air Walk" test to be run to ascertain
1804 — that the device is functioning well and that all
the relevant sensors are giving the correct signals Rosemary Vanguard | 38 yrs | Spinal Cord Injury
Completed: 3/10 sessions
Vitals: BP (normal), Sugar (low), Heart Rate (erratic)

Injury sustained during a fall. Spinal cord T4 mild ∽ 2802
fracture. Left tilt when trying to walk
**Target: Regular walk for independent activities
(cooking, shopping etc). No sports or strenuous
activities planned.**

Patient ID
2018233345

SCI-FAP Score

| 1 | 2 | 3 | 4 | 5 | 6 | 7 | 8 | 9 | 10 |
|---|---|---|---|---|---|---|---|---|---|
| 2000 | 1800 | 1750 | 1600 | 1400 | 1400 | 1200 | 1000 | 750 | 620 |
| 2050 | 1900 | 1800 | 1580 | | | | | | |

2804

Review ⟵ 2806

APPARATUS AND SYSTEM FOR LIMB REHABILITATION

CROSS REFERENCE TO RELATED APPLICATIONS

This application claims priority to Indian provisional application 201741045051 filed on Dec. 14, 2017. The disclosure is hereby incorporated by this reference in its entirety for all of its teachings.

FIELD OF THE INVENTION

The present invention relates to a robotic apparatus and a system for limb rehabilitation. More specifically robotic system that helps regain gait in a human being.

BACKGROUND OF THE INVENTION

There are over 10 million persons with locomotion disorders in worldwide, caused by various life changing incidents such as stroke, spinal cord injury, war injuries or other diseases. As a result of loss of the physical mobility, the affected person cannot carry out his desired or even day to day activities with full participation or in worse cases resulting in complete loss of mobility. Further the affected persons are prone to suffer from severe emotional trauma and depression as a result of their condition.

Various assistive devices have been developed over last decade for assisting the persons suffering from the mobility disorders with an objective to help the disabled person to regain the ability to stand and walk, and also minimize the requirement of intensive therapist dependent training. One category of assistive devices that help in rehabilitation is exoskeleton in nature. A powered exoskeleton device is a wearable mobile machine that is powered by a system of electric motors or pneumatics or levers, or hydraulics, or a combination of technologies that allow for limb movement with increased strength and endurance. However, these devices have major drawbacks and are limiting their use as both therapeutic as well as a mobility device. The drawbacks include, large 'filtering out' of needy patients due to lack of safety, and lack of their ability to handle the system. Critical 'Early Intervention' time is lost until patients become eligible for therapy, their ability to improve from therapy significantly reduces. lack of guaranteed fall safety, challenges in donning and doffing, slow speed, limited range, difficulty in transferring, rough movement, high dependency on the operating therapist, unequal pressure distribution, potential skin issues due to the hardness of the materials used and the high costs.

Further the patient/individual/user face the risk of falling and also the heavy exoskeleton device makes it inconvenient to use. In addition, the tedious manual effort is needed to support/strap patient into the exoskeleton for rehabilitation.

In view of the foregoing, there is a need for a robotic exoskeleton assisted rehabilitation system that is 100% fall safe, which enables early intervention, even while walking with the exoskeleton device, light in weight and easy to use and move around and most importantly cost effective as compared to the systems that are presently available.

SUMMARY

The instant application discloses a robotic lower limb rehabilitation apparatus and system. The robotic limb rehabilitation apparatus comprises of a mobile-frame, dynamic weight unloading mechanism and lower extremity exoskeleton device. In one embodiment, the mobile-frame structure comprises of left (first) and right (second) vertical structural support members connected by a horizontal cross bar/beam to which a boom arm assembly is attached. In another embodiment, a harness is fixed to the boom arm. In another embodiment, a flexible rope is attached to the boom arm to hold the harness. In one embodiment, the harness helps in supporting and securing the torso and pelvic region of an injured patient/individual/user to provide 100% fall safe limb rehabilitation.

In another embodiment, the dynamic weight unloading mechanism is operated using a centrally located ball screw arrangement which drives an upper plate. The lower plate is connected via helical coil springs. Both upper and lower plates are connected on the frame via guide rails. In one embodiment, the lower extremity exoskeleton device comprises of one lower body interface, four right and left shank members with clamps, two sets of motorized joints and one of set of unpowered joint. In another embodiment, the ankle joints may also be powered through the lower extremity exoskeleton device. In one embodiment, a lower limb exoskeleton frame is secured on to the lower extremity of the patient/individual/user and the exoskeleton works in conjunction with the mobile-frame, the harness for weight support and sensors for monitoring/adjusting/analyzing/feedback on the lower limb movements.

An object of the present invention is to relieve the patient of carrying the weight and inertia of the battery, computer, and motor while undergoing rehabilitation. In another embodiment of this invention, the weight and inertia of the battery and computer are removed from the patient's body, while the motors are still carried on body. In another embodiment of this invention, the weight and inertia of the battery, computer, and the locomotion rehab device is able to be maximally lightweight.

In one embodiment, a robotic management module and system is implemented using a processor, device and hardware to optimize the exercise for a user and that controls the robotic lower limb rehabilitation apparatus. In another embodiment, a closed loop control system is implemented to deliver the prescribed therapy protocols to the patient. Multiple sensors are used to detect the patient gait behavior and effort that is attached to the lower extremity exoskeleton device and the mobile-frame sensors, and based on the feedback received; a proprietary control algorithm sends the corrective actuation signals to the motors. A sensor based input from the lower extremity exoskeleton device and the robotic lower limb rehabilitation apparatus is collected in the database and used by artificial intelligence module for calculations for evaluation and recommendation of the optimal exercise routine and effect of the routine for a specific user.

In one embodiment, a cloud based software system or internet based system is used for data gathering, analysis and control of the robotic limb rehabilitation apparatus. In one embodiment, the mobile frame is self-propelled by motors. The lower extremity exoskeleton device based sensor and sensor is based on mobile frame, rope tilt sensor, detects the patient motion, and a proprietary control algorithm actuates the mobile frame drive motors such that it intelligently follows the patient during rehabilitation exercise.

Other features will be apparent from the accompanying drawings and from the detailed description that follows.

BRIEF DESCRIPTION OF THE DRAWINGS

The other objects, features and advantages will occur to those skilled in the art from the following description of the preferred embodiment and the accompanying drawings in which.

Figure 1:
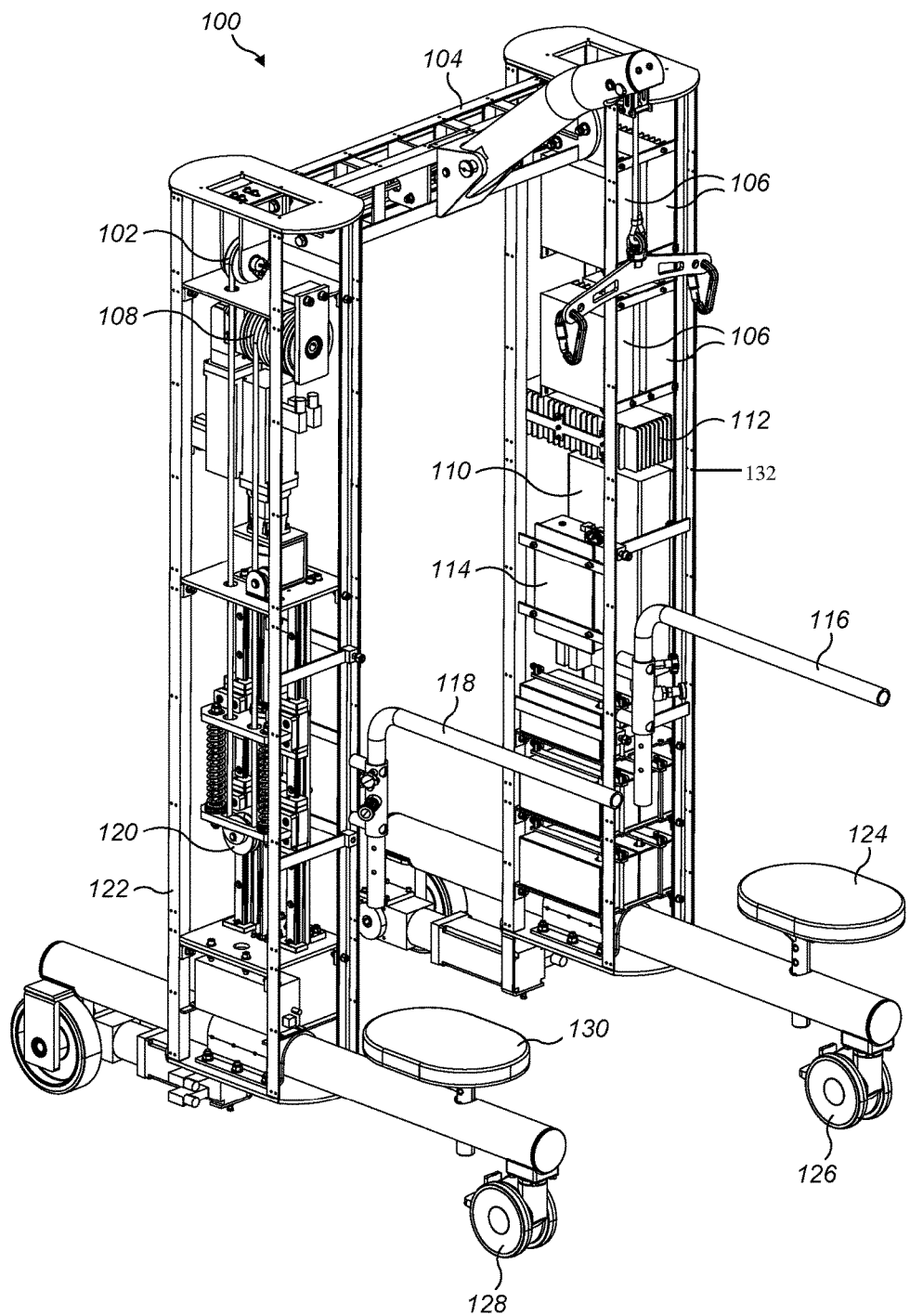
FIG. 1 illustrates a schematic perspective view of a robotic limb rehabilitation apparatus for limb rehabilitation depicting arrangement of a Mobile-Frame, according to an embodiment of the present invention.

Other features of the present embodiments will be apparent from the accompanying drawings and from the detailed description that follows.

DETAILED DESCRIPTION

Several systems and methods for using a robotic limb rehabilitation apparatus to control the robotic limb rehabilitation apparatus are disclosed. There is a need for evaluation and treatment of patients with short- or long-term physical and/or cognitive impairments and disabilities that result from musculoskeletal conditions (neck or back pain, or sports or work injuries), neurological conditions (stroke, brain injury or spinal cord injury) or medical other conditions. The goal is to decrease pain and enhance performance without surgery. Instant robotic limb rehabilitation apparatus and software system with feedback mechanism helps user/patients with treatment methods such as regaining a proper gait. The present invention relates to a 100% fall-safe mechanized system for locomotive rehabilitation and gait training. There are many rehabilitation areas that various modifications and changes may be made to these embodiments without departing from the broader spirit and scope of the various embodiments.

In this disclosure, rehabilitation refers to the process of enabling a patient to do a "powered sit-to-stand", aided and unaided standing, re-learning to walk at a specified minimum speed and with an appropriate gait. An object of the present invention is to provide a robotic lower limb rehabilitation apparatus that uses lightweight materials like aluminum or composite materials or other similar materials. The present invention discloses a mobile-frame for robotic lower limb rehabilitation apparatus with a means for remotely controlling by the therapists, users and doctors.

Many conditions require this equipment as there are issues with Gait analysis or debilitating diseases such as spinal cord injury, stroke, diabetes, neural diseases, injury, accidents, Stroke, Spinal Cord Injury, Traumatic Brain Injury, Multiple Sclerosis, Osteoarthritis, Rheumatoid Arthritis, Limb Loss, and Back Pain etc., but not limited to these. Gait analysis involves measurements that involve temporal/spatial consisting of speed, the length of the rhythm, pitch etc., kinematics, markerless gait capture, pressure measurement, kinetics that involve study of forces in the production of movements and dynamic electromyography. This use of kinetics, however, does not result in information for individual muscles but muscle groups, such as the extensor or flexors of the limb. To detect the activity and contribution of individual muscles to movement, it is necessary to investigate the electrical activity of muscles. The sensors attached to the foot pad and knee joints braces and the machine sensors in this current application allows us to get feedback on not only for the gait analysis but also for the effect of exercise on big muscles such as the extensor or flexors of the limb. The reading may not be limited to only these muscle groups but may also include back and hip muscles etc.

A plurality of (embedded and non-embedded) sensors for smart assistance (help as needed by patient) and operation of the robotic lower limb rehabilitation apparatus. An object of the present invention is to provide a novel design for a robotic limb rehabilitation apparatus and software system. The robotic limb rehabilitation apparatus and software system is a combination of dynamic weight unloading system, mobile-frame, lower extremity exoskeleton device and harness to support the upper body to work in conjunction with common power, controls, optimized actuators and motors that are capable of enhancing recovery progress.

FIG. 1 illustrates a schematic perspective view of the robotic limb rehabilitation apparatus depicting arrangement of a mobile-frame and the dynamic weight unloading system, according to an embodiment of the present invention. The Mobile-Frame (100) comprises a right vertical support member (122) and a left vertical support member (132) affixed on a moving platform. The right vertical support member (122) and the left vertical support member (132) are connected to each other by a horizontal cross bar (104). Further, the mobile-frame (100) also comprises a boom arm assembly (304) which is connected to the horizontal cross bar (104). The mobile-frame also include at least one therapist Seat (124 and 130) affixed on the moving platform to enable the therapist to be seated comfortably while assisting the patient either from the right side or left side. According to an embodiment of the present invention, the mobile-frame (100) is manufactured using a lightweight material such as aluminum or any composite materials or any such similar materials.

Figure 6:
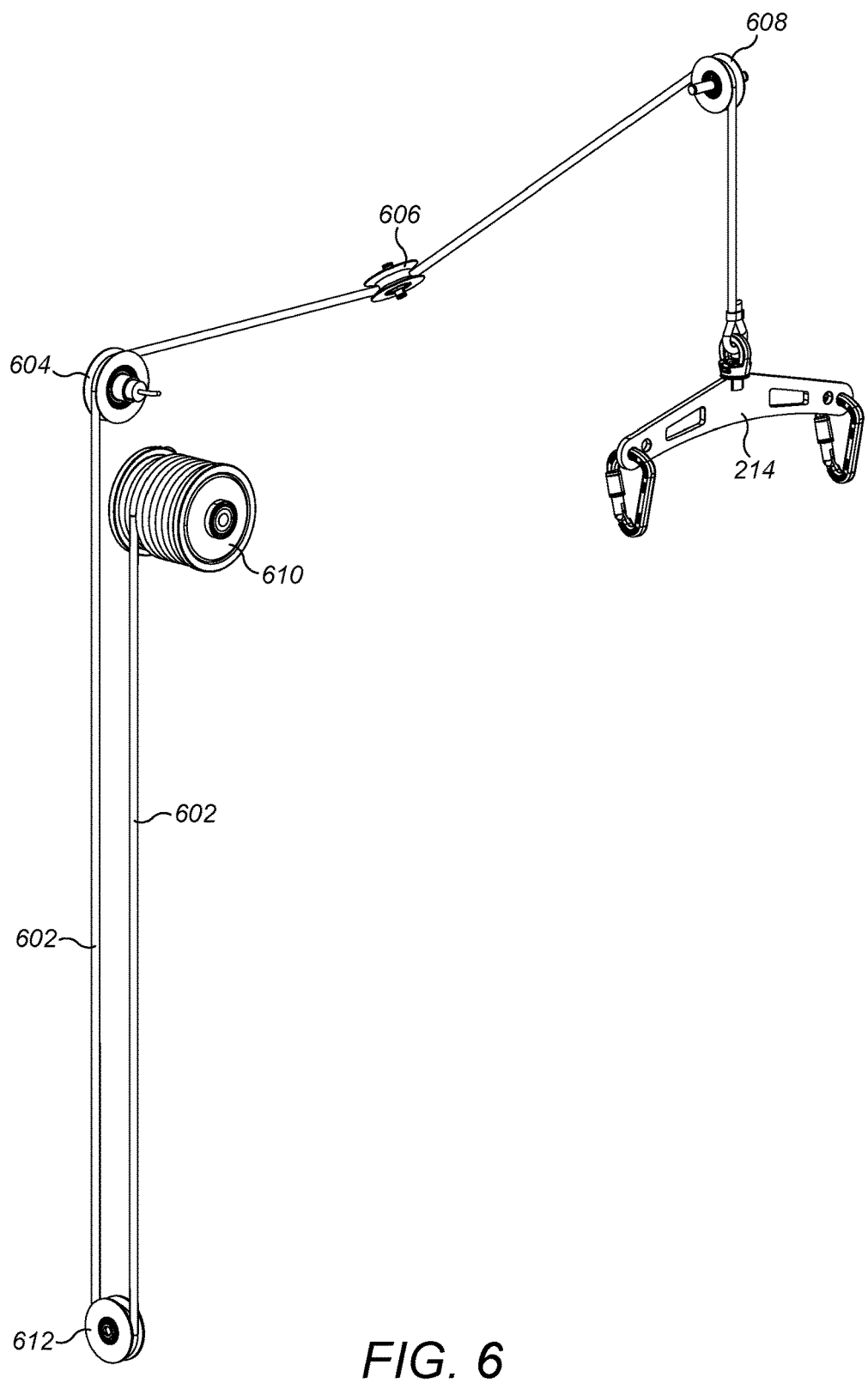
FIG. 6 illustrates a schematic arrangement of the harness pulley system, according an embodiment of the present invention.

The first vertical support member (122) of the mobile-frame (100) includes Pulley 1 (120), Pulley 2 (102) and a Winch Assembly (108) as shown in FIGS. 1 and 6. The mobile-frame (100) also includes two additional Pulleys—Pulley 3 (606) in the cross bar (104) and Pulley 4 (608) in the boom arm assembly (304), as shown in FIG. 6 wherein all the pulleys are connected via flexible rope arrangement.

Figure 2:
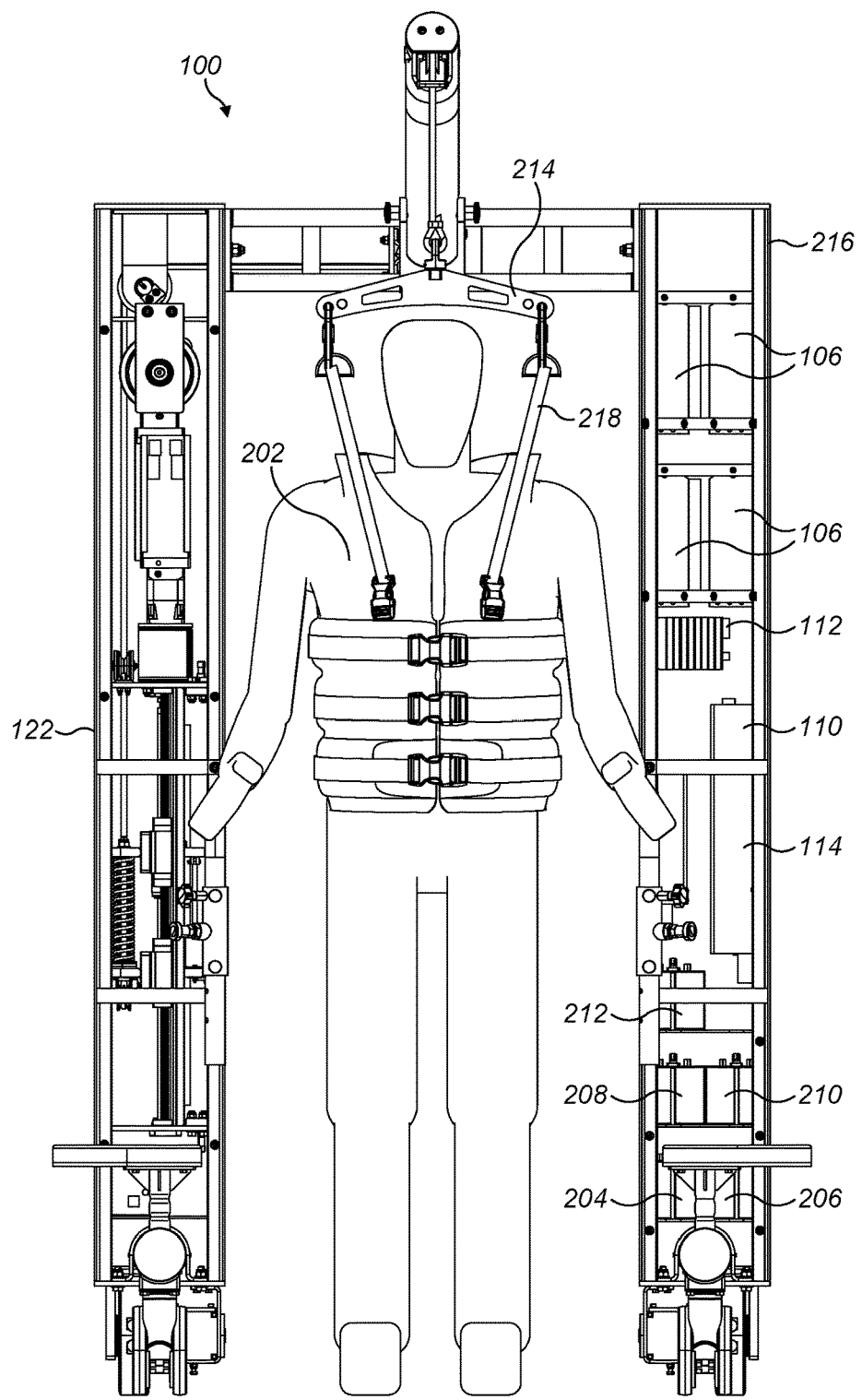
FIG. 2 illustrates a schematic front view of a robotic limb rehabilitation apparatus with a patient, according to an embodiment of the present invention.

The left vertical support member (132) of the mobile-frame (100) houses at least four servo drives (106) for electric motors, an electronic controller (112), at least one inverter (110), at least one battery charger (114) and one or more batteries (212, 208, 210, 204, 206) (as shown in FIG. 2) to run the control function and also provide power to the mobile-frame and exoskeleton.

The mobile-frame includes a pair of height adjustment arm support (116, 118) attached to the right and left vertical support member (122, 132) as a support for the patient to hold on during the rehabilitation. The height of adjustment arm support (116,118) can be adjusted at least to five levels.

The mobile-frame (100) is a movable frame and movability of the platform is aided by two sets of wheels—left and right caster wheel set (126 and 128) (Front Wheel set) and left and right rear wheel set (314) (Rear Wheel set) (refer FIGS. 1, 3 and 4) attached to the wheel support members. The front wheel set (126 and 128) is for steering the mobile-frame (100) and while the rear wheel set (314), powered by a motor on each wheel, is for driving the mobile-frame (100) with the patient/individual/user during rehabilitation. The movement of the mobile-frame (100) is controlled by a remote-controlled device or computer device present with the therapist, doctor or patient.

FIG. 2 illustrates a schematic front view of the mobile-frame (100) with a patient in standing position, according to an embodiment of the present invention. The mobile-frame (100) provides support to a patient (202) who is in a standing position using a spreader bar (214), a harness (218) for weight support, and the pair of height adjustment arm support (116,118) attached to the right and left side vertical structural support members (122 and 132).

According to an embodiment of the present invention, a harness (218) for weight support, is provided to support/secure the torso and pelvic region of an injured individual/patient/user (202), wherein the material used for harness is made from a human skin friendly material or a similar padded material.

Figure 3:
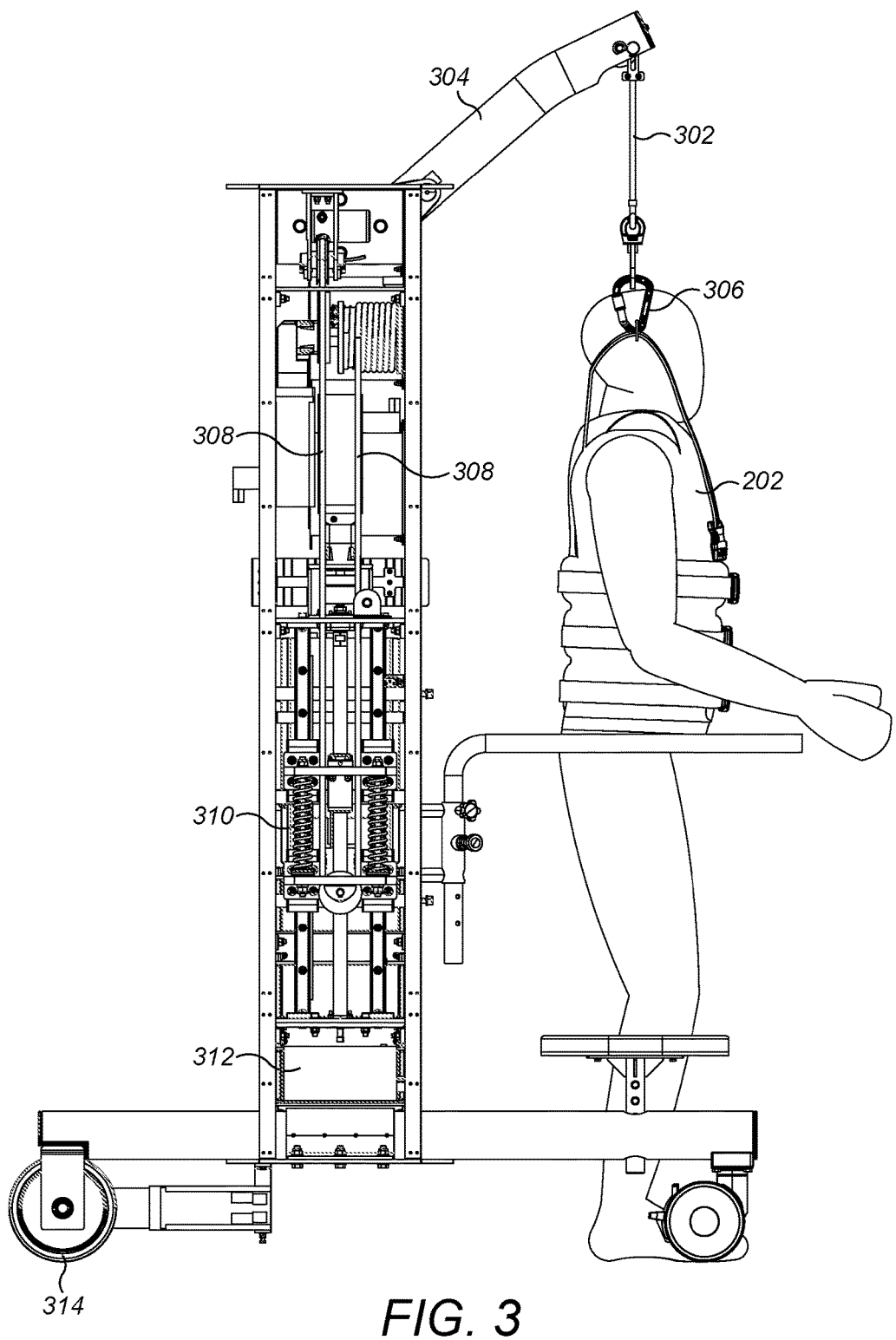
FIG. 3 illustrates schematic right-side view of a robotic limb rehabilitation apparatus with a patient, depicting a harness locking mechanism, according an embodiment of the present invention.

FIG. 3 illustrates a schematic right-side view of the mobile-frame with a patient, depicting a harness locking mechanism, according to an embodiment of the present invention. The mobile-frame particularly shows at least a pair of spring (310) in the weight unloading mechanism, a flexible rope arrangement (308), a motorized rear wheel (314), a brake resistor (312) along with the boom arm (304), the harness locking mechanism (306), the therapist seat (130), the height adjustable arm support (118) and the patient/individual/user (202).

According to an embodiment of the present invention, the flexible rope arrangement (308) is used as a means for operating the weight unloading mechanism. The pair of springs (310) is provided to aid in the operation of the weight unloading mechanism. The brake resistor (312) is provided for heat dissipation of regenerated power during fall arrest (314).

Figure 4A:
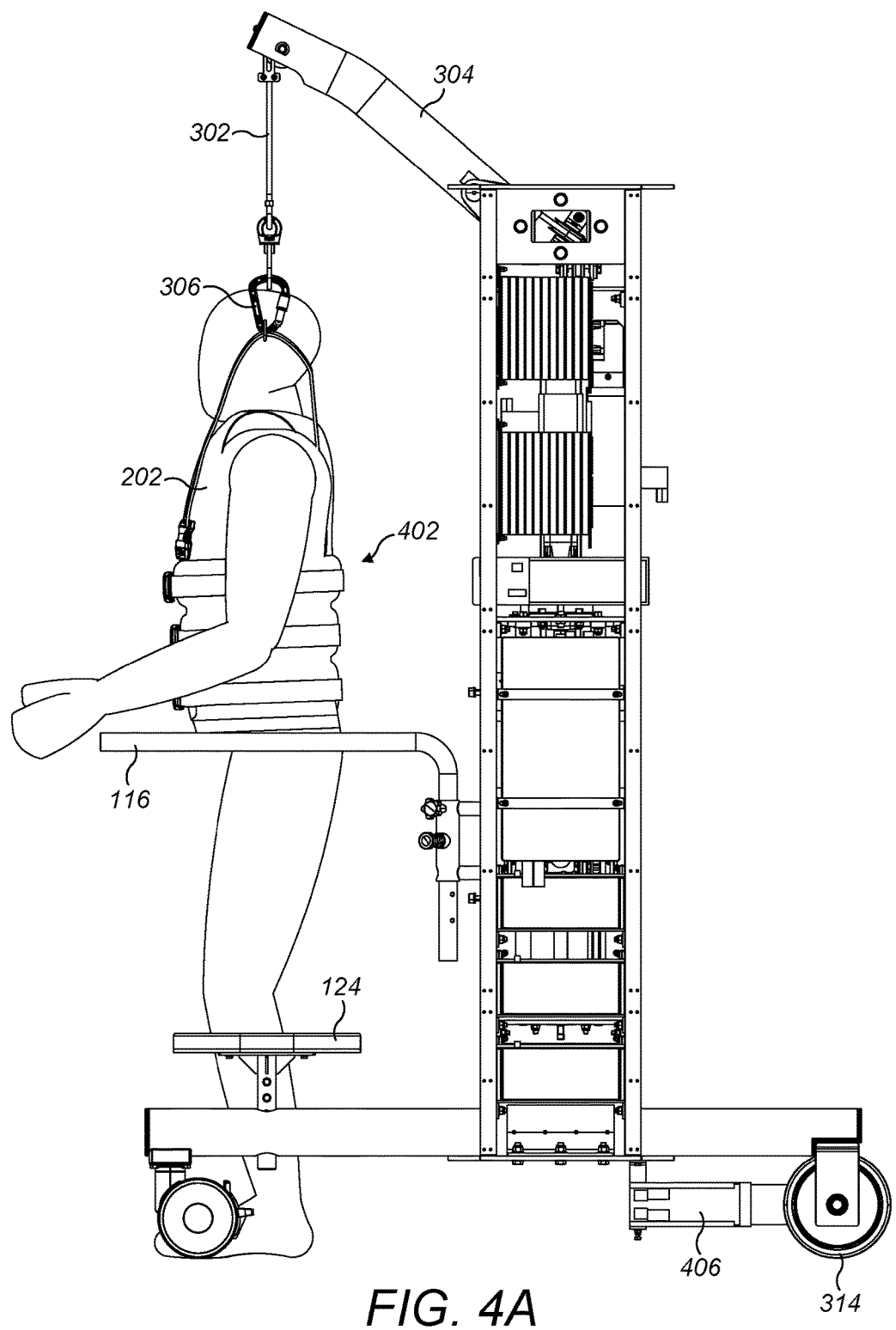
FIG. 4A illustrates schematic left side view of robotic limb rehabilitation apparatus depicting a harness worn by the patient to prevent fall, according an embodiment of the present invention.
Figure 4B:
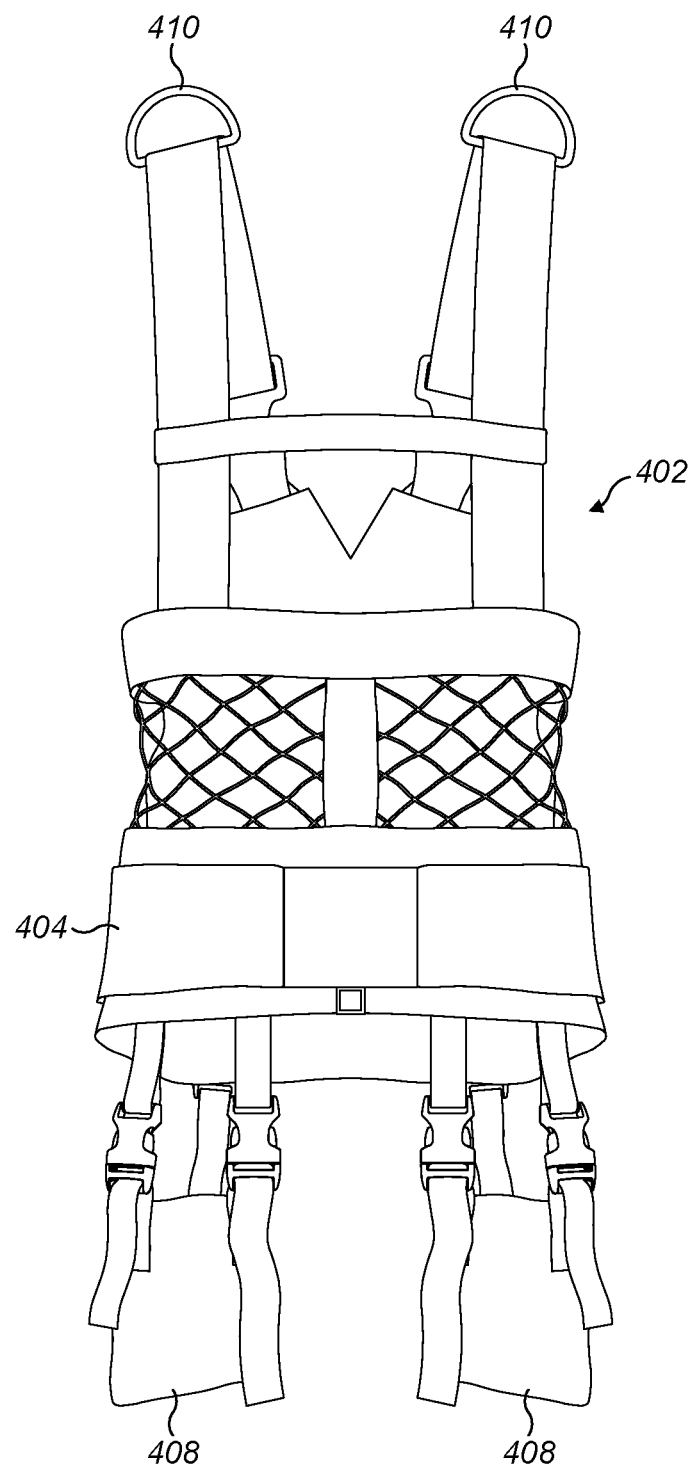
FIG. 4B refers to harness that is to be worn by user.

FIGS. 4A and 4B illustrates a schematic left side view of the Mobile-Frame depicting a harness (218) worn by the patient (202) to prevent fall, according to an embodiment of the present invention. The Mobile-Frame particularly shows the harness (218), wherein the harness (208) comprises of a pair of locations (410 in FIG. 4B) for locking the harness to the spreader bar (214), a torso securing strap (404) and a pelvis securing straps (408), along with the boom arm assembly (132), the harness locking mechanism (306), the therapist seat (124), the height adjustable arm support (116), the patient/individual/user (202) and the motorized rear wheel (314) with a motor (406).

According to an embodiment of the present invention, the harness (218) is connected to the spreader bar (214) with the help of harness locking mechanism (306) at the two locations (410) which in turn connected to the Boom arm (304) using a flexible rope (302). The torso securing strap (404) and the pelvis securing straps (408) are provided in the harness to secure the patients torso region and pelvis region. The harness disclosed herein provides for an easy donning/doffing on the patient/individual/user thereby reducing time and discomfort experienced by the patient/individual/user.

According to an embodiment of the present invention, the motor (406) drives the rear wheel (314) of the mobile-frame enabling it to be moved around while operating the mobile-frame by the therapist.

Figure 5A:
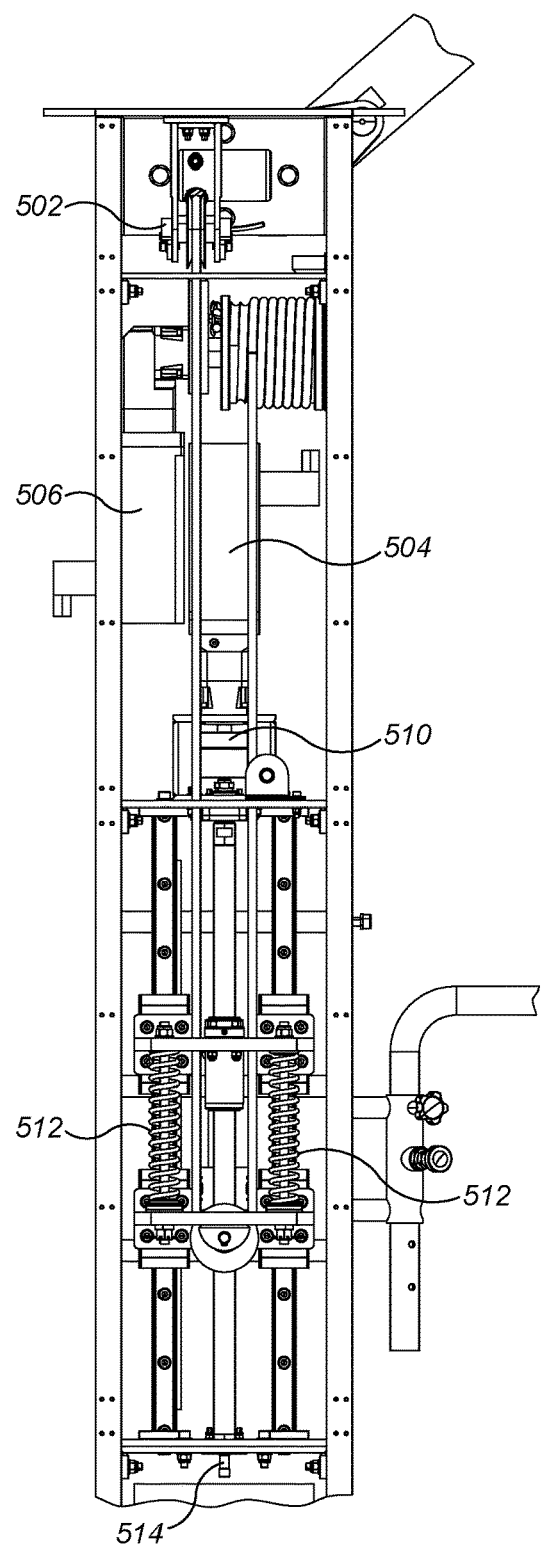
FIG. 5A illustrates a schematic front view of the right vertical support member.
Figure 5B:
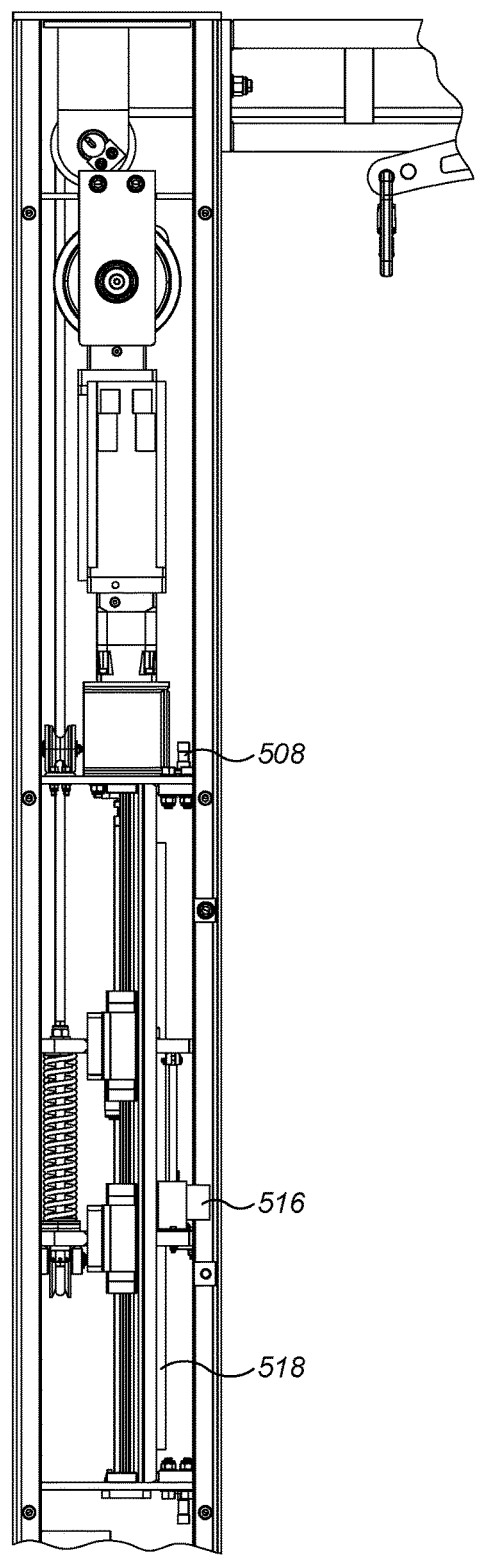
FIG. 5B illustrates a schematic side view of the right vertical support member.

FIGS. 5A and 5B illustrates a schematic side view and front view (520) of the right vertical support member (102) of the mobile-frame (100), according to an embodiment of the present invention. The right vertical support member (102) of the mobile-frame (100) comprises of a cylindrical load cell (502), a motor (504) to control ball screw, a motor (506) to control a winch drum, a coupling (510) arrangement, a pair of springs (512), a pair of ultrasonic sensors (514, 508) and a string potentiometer (516).

According to an embodiment of the present invention, the cylindrical load cell (502) is provided to measure the tension on the flexible rope (502) member passing over it. A pair of motors (504 and 506) is provided to control the ball screw and the winch drum. Further the motors (504 and 506) are connected to the arrangement below an upper support plate (712) with the help of the coupling (510). The pair of ultrasonic sensor (514 and 508) is provided therein, one at the upper support plate (712) and other at a lower support plate (714) to sense the movement of the carriage. Additionally, a string potentiometer (516) is provided to detect and measure the linear position. In addition a linear encoder (518) is used in the design for detecting the rope movement speed to arrest fall.

FIG. 6 illustrates a schematic arrangement of rope assembly (600) of the dynamic weight unloading mechanism, according to an embodiment of the present invention. The rope assembly (600) of the dynamic weight unloading mechanism comprises of a pulley 1 (612) on sliding carriage of the dynamic weight of unloading mechanism, a pulley 2 (604) in the right vertical structural support member (122), a pulley 3 (606) housed in the horizontal cross bar (104), a pulley 4 (608) housed in the boom arm assembly (304), a flexible rope (602), a spreader bar (214) and a winch assembly (610 or 108).

According to an embodiment of the present invention, the flexible rope (602) arrangement runs over the series of four pulleys (612, 604,606, 608). The rope assembly (600) arrangement involves attaching the flexible rope at one end to the motorized winch assembly (610) passes through the pulley housed in the boom arm (304) and connected to the Spreader Bar (214) at the other end.

Figure 7A:
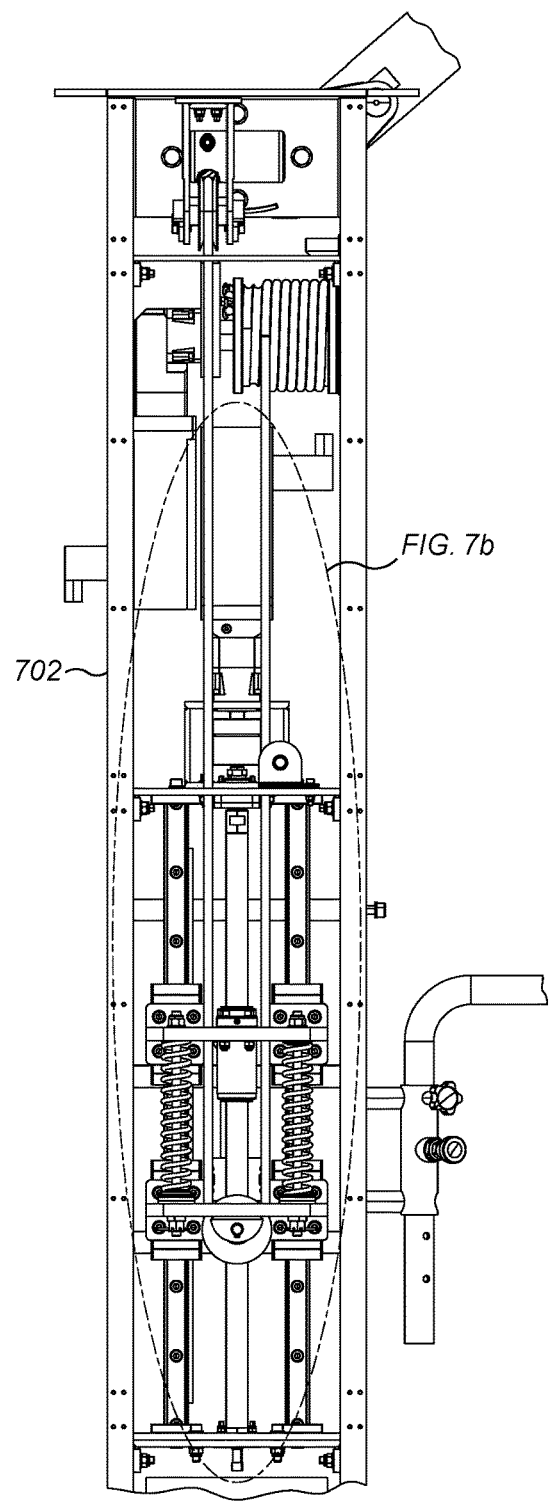
FIG. 7A illustrates a schematic arrangement of the Dynamic Weight Unloading Mechanism for expansion mode for FIG. 7B for more details, according an embodiment of the present invention.
Figure 7B:
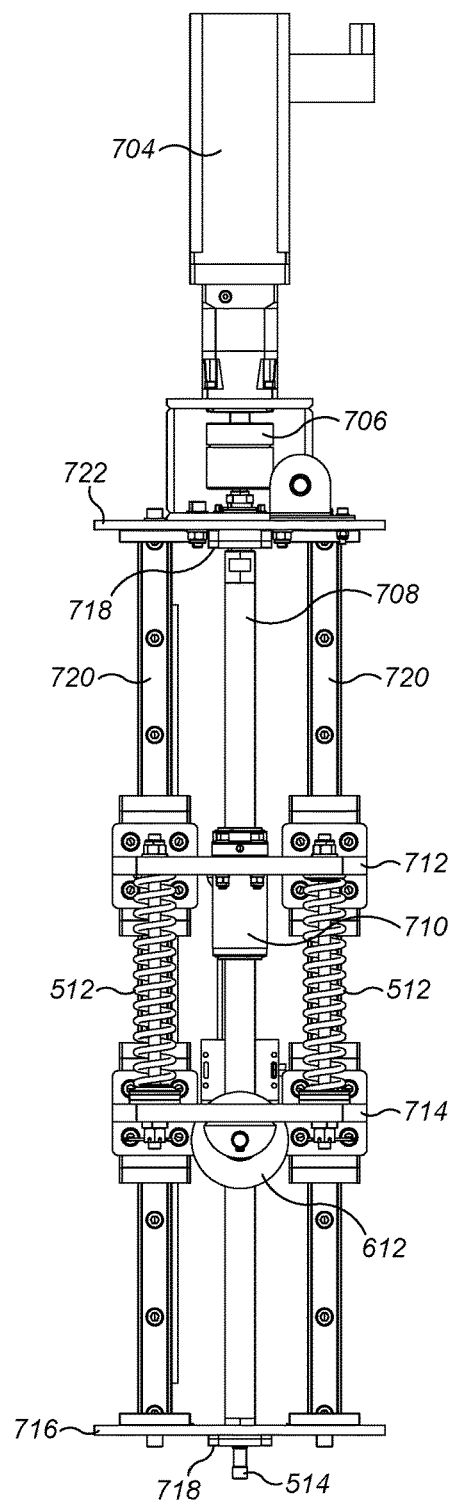

A portion of FIG. 7A is expended as FIG. 7B to show more details. FIGS. 7A and 7B illustrates a schematic arrangement of the dynamic weight unloading mechanism (702). The dynamic weight unloading mechanism (702) comprises of a ball screw (708), a motor (704) to control the ball screw (708), a ball nut (710), a coupling (706), a pulley (612), an ultrasonic sensor (514), a guide rails (720), an end support (716) at upper and lower support plate, an upper spring support plate (712) with the ball nut (710), and a lower spring support plate (714) with pulley (612).

The servo motor (704) is coupled to the upper support plate (722) with the help of coupling (706). The two guide rails (720) along with one centrally located ball screw (708) is connected with the upper support plate (722) and lower support plate (716) through the spring arrangement. The carriage is enabled to slide on two guide rails (720) with two spring supported plate (512). The movement of the carriage upward and downward is controlled by the rotation of the ball nut (710) on ball screw (708). The ball nut (710) is connected to the upper spring support plate (712) and the ball screw (708) passes through the same. The pulley (612) is attached to the lower spring support plate (714) through the rope (302) from the winch (610) is passed. The movement of the support plates both at the upper and lower is detected using the two ultrasonic sensors (514, 508) provided thereunder. A means for measuring the movement of the carriage is provided with the help of linear encoder.

Figure 8:
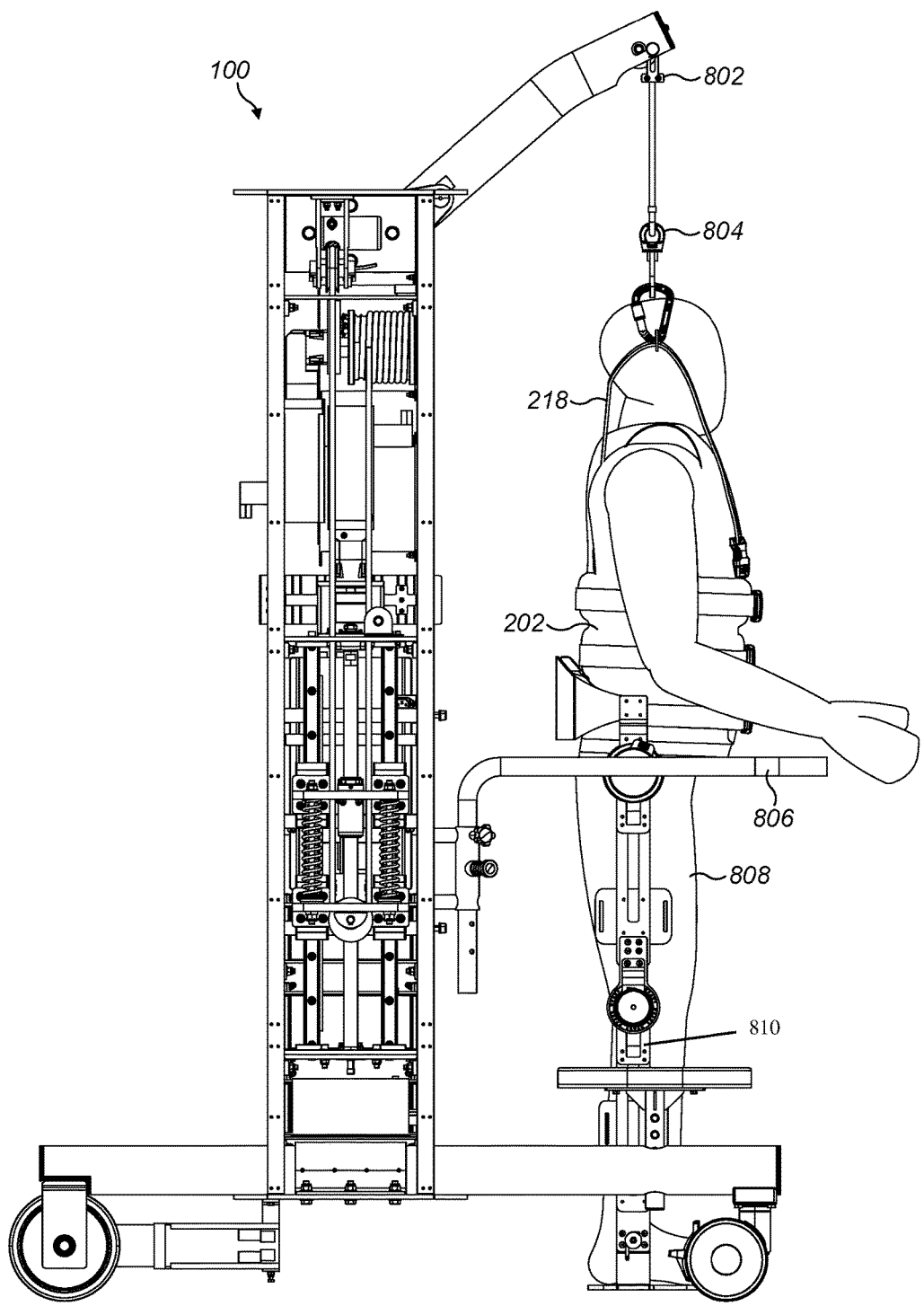
FIG. 8 shows the entire robotic limb rehabilitation apparatus with user secured with harness and lower extremity exoskeleton device.

FIG. 8 illustrates a schematic arrangement of the lower extremity exoskeleton device and patient secured with the harness, according to an embodiment of the present invention. The apparatus comprises of the mobile-frame (100), a weight support harness (218), and a powered lower extremity exoskeleton device (810), wherein the patient/user (204) is secured by the lower extremity exoskeleton device (810).

In the lower extremity exoskeleton device, the first set of motorized joint (804/1004) connects with the waist clamp to the upper shank around the hip area of the patient/user (204).

The second set of motorized joint (806/1008) connects with the upper shank to the lower shank around the knee area of the patient/user (204).

Figure 9:
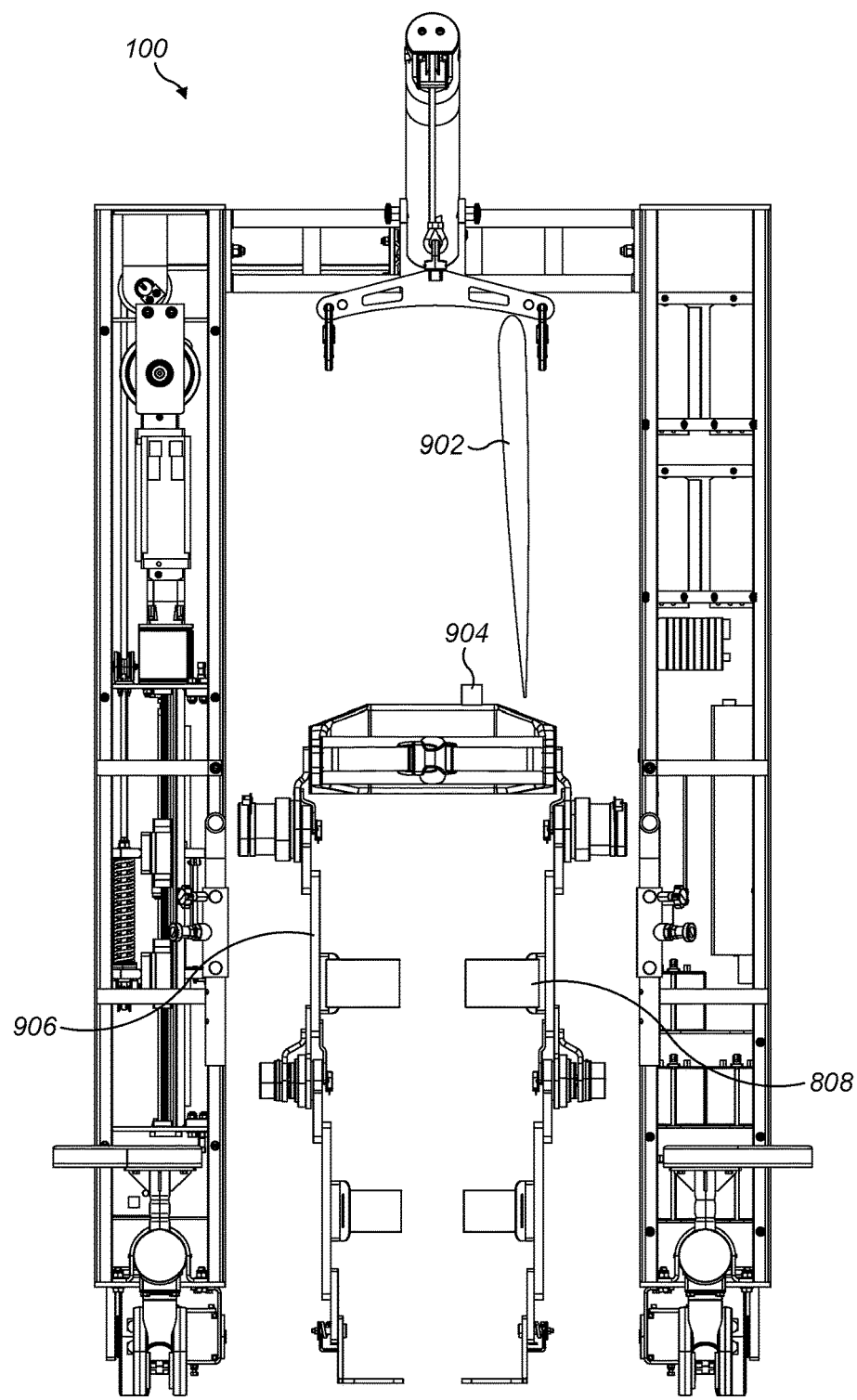
FIG. 9 shows the entire robotic limb rehabilitation apparatus without user to show a belt and lower extremity exoskeleton device.

FIG. 9 shows a schematic diagram of the lower extremity exoskeleton device with a waist clamp ensemble. A connecting port (904) ensures supply of power and signals from the batteries and computers housed in mobile frame (100) to the motors and sensors via tethered cable (902). The adjustable height support 906 allows accommodating for height adjustment for patients of different heights.

Figure 10:
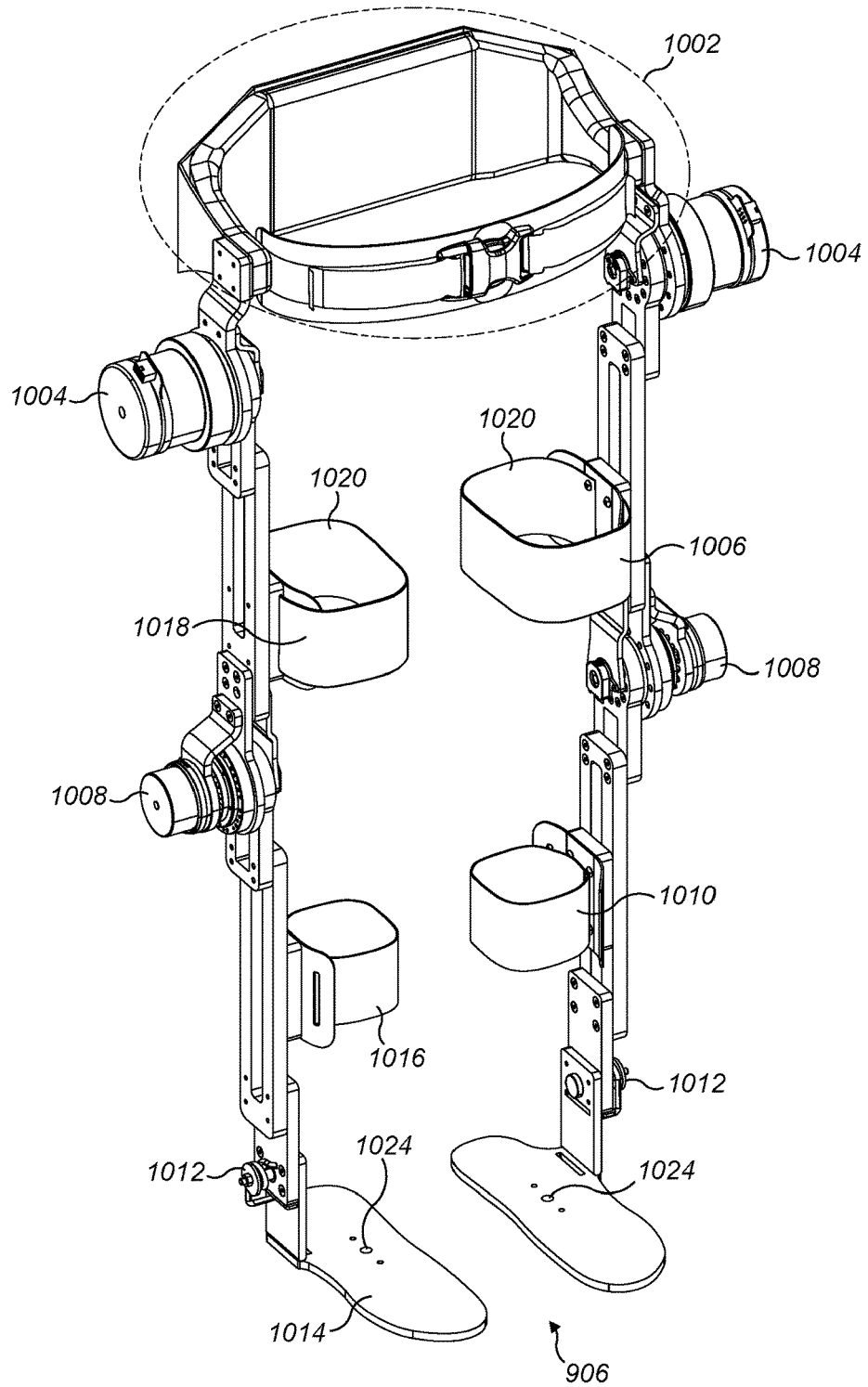
FIG. 10 illustrates a schematic arrangement of the lower extremity exoskeleton device with waist clamp, according to one embodiment.

FIG. 10 shows details of the lower extremity exoskeleton device. lower extremity exoskeleton device comprises of a waist clamp mechanism (1002), a pair of motorized hip joints (1004), a right upper shank clamp (1020), a left upper shank clamp (1020), a pair of motorized knee joints (1008), a right lower shank clamp (1016), a left lower shank clamp (1010), an unpowered ankle joint (1012) and a foot pad (1014). The foot rests show sensors 1024.

The lower extremity exoskeleton device comprises of a pair of motors (1004 and 1008) wherein the motor (1004) controls the hip joints and the motor (1008) controls the knee joint. The third joint connecting the shank clamps (1018 and 1008) to the foot pad (1014) is not motorized and arranged to adjust as per the user's position.

Figure 11:
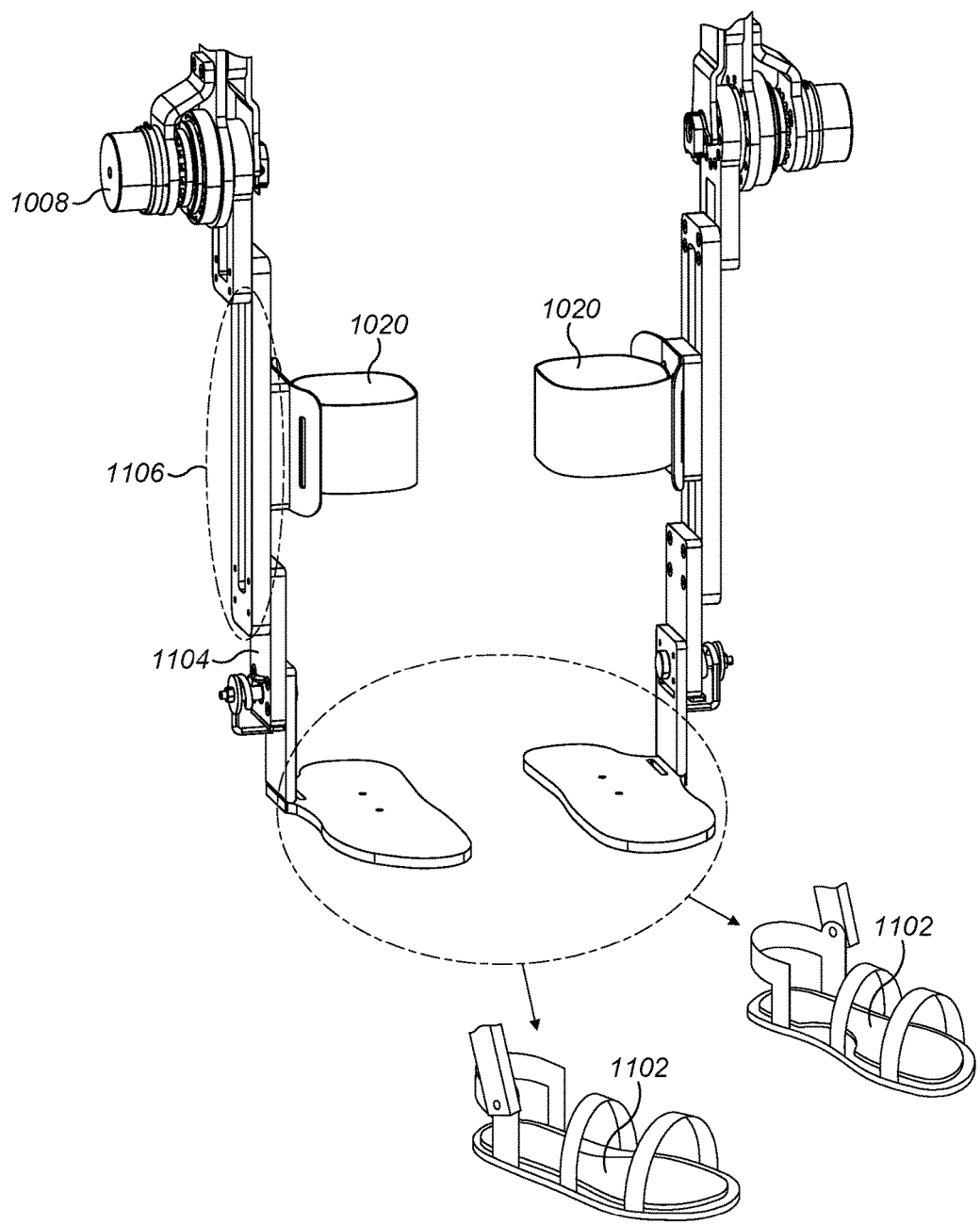
FIG. 11 illustrates a schematic arrangement of the lower extremity exoskeleton device with a height adjusting mechanism, according to one embodiment.

FIG. 11 illustrates a schematic arrangement of a height adjusting mechanism, in the lower extremity exoskeleton device. The height adjusting mechanism is provided which includes height adjustable slots (1106 and 1104) between the motorized knee joint and the lower shank at the right side and the left side.

The motorized knee joint (1008) helps in the movement of legs as controlled by the therapist. Further, based on the height of the patient/user, the height of the lower shanks can be adjusted with the help of the multiple adjustable slots (1020/1106) provided to adjust the height both at the right side lower shank and the left side lower shank.

Figure 12:
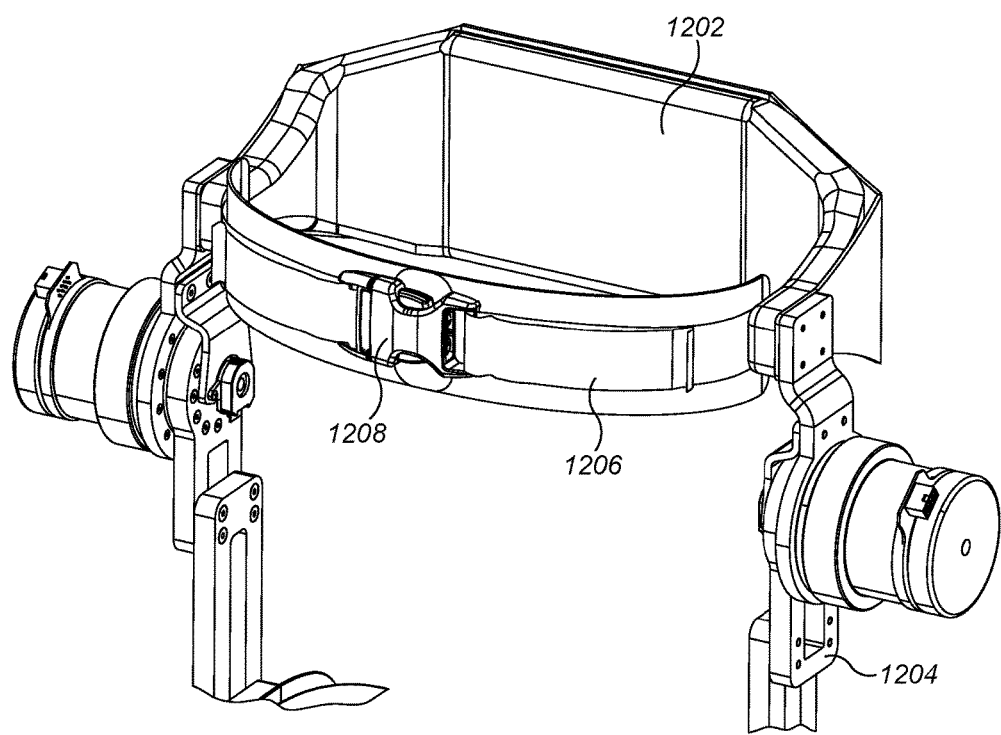
FIG. 12 expands the waist clamp of FIG. 10 to show more details.

FIG. 12 illustrates a schematic arrangement of the waist clamp (1002) in detail, according to an embodiment of the present invention. The waist clamp (1002) comprises of a waist support (1206), an adjustable length strap (1208) with padding, and a strap locking mechanism (1202). Additionally, the shank clamps (1204) are provided with a padding/cushion, and a height adjustment release button.

In one scenario, the user/patient fails to control voluntary movement may be due to damage to a portion of the brain or spinal cord for example in the case of Spasticity, car crash, or other symptoms. In order to overcome such situation, the robotic lower limb rehabilitation apparatus and system is adapted with a smart control unit which comprises a plurality of sensors and a controlling module. The plurality of sensors detects the unusual movements/actions of the patient and provides a signal to the controlling module. The controlling module process the signals and converts the operation into a transparent mode on identifying the unusual movement or predefined conditions, in order to avoid any harm to the patient or robotic lower limb rehabilitation apparatus.

Figure 13:
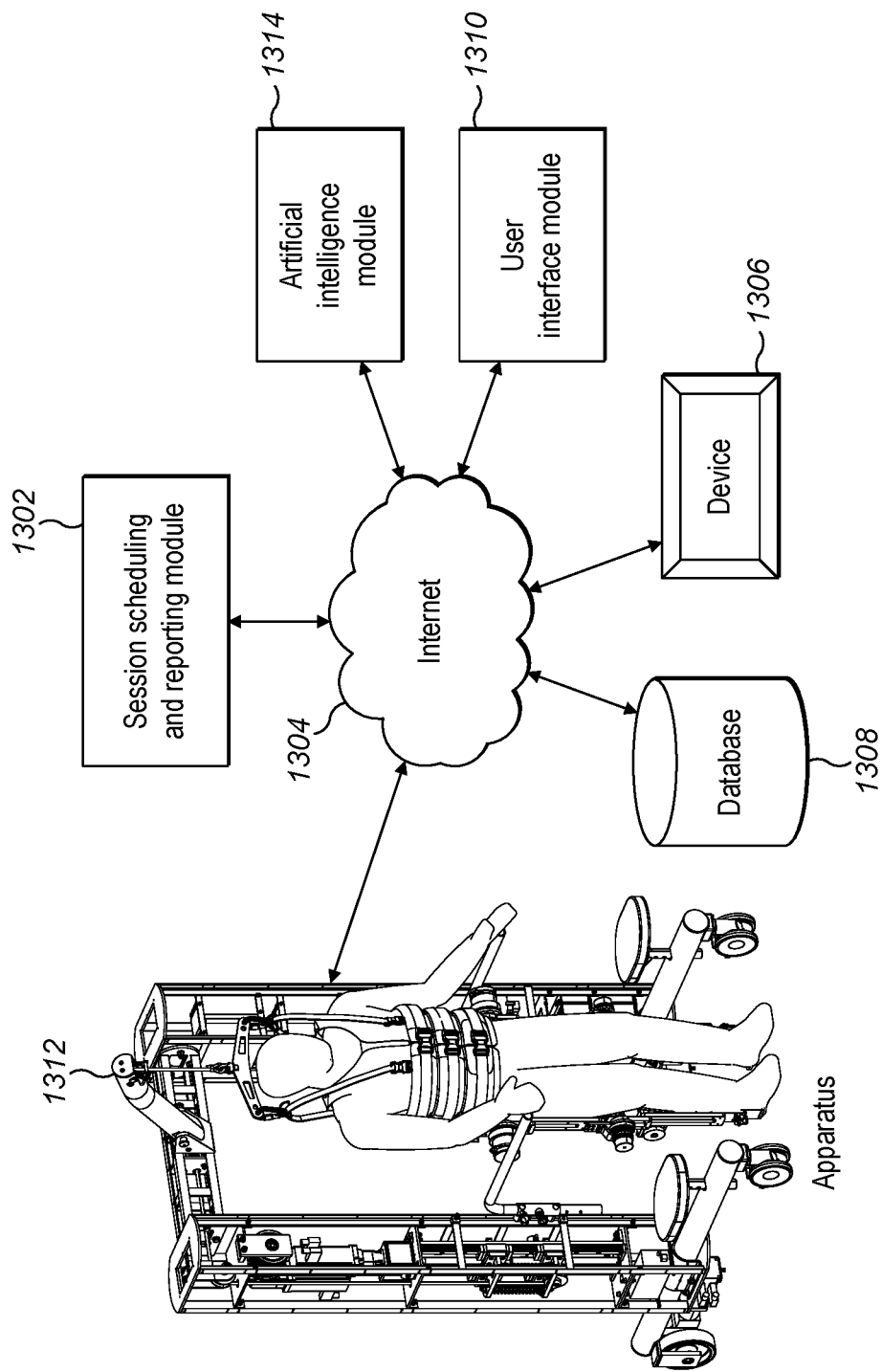
FIG. 13 shows an integrated robotic limb rehabilitation apparatus and system, in one embodiment.

FIG. 13 shows a system view of the robotic lower limb rehabilitation apparatus 1312 and connectivity with software. Internet 1304 connects all elements of the software to the hardware the robotic lower limb rehabilitation apparatus 1312. Session scheduling and reporting module 1302 controls the robotic lower limb rehabilitation apparatus and the sensors, loads and the motors to help the patient to optimize the exercise routine. Artificial intelligence module 1314 accommodates and calculates optimal exercise routine for the said user and also sends feedback to doctor, therapist and patient regarding new exercise schedule and improvements. Sensors that are embedded in the robotic lower limb rehabilitation apparatus allow the artificial intelligence module 1314 to gather information while the user is using it and based on prior exercises. User interface module 1310 allows user to see what the doctor and the therapist have designed for that particular day for them to follow. Also it gives them a comprehensive view of the therapy regiment. Database 1308 enables all stake holders to store and retrieve data in real time as well as historical data. All modules use input from the database 1308 and store information for future use. Device 1306 may be used by therapist or doctor or patient for input and viewing. The following figures when described will cover these elements in detail. Devices may be mobile device or computers.

Figure 14:
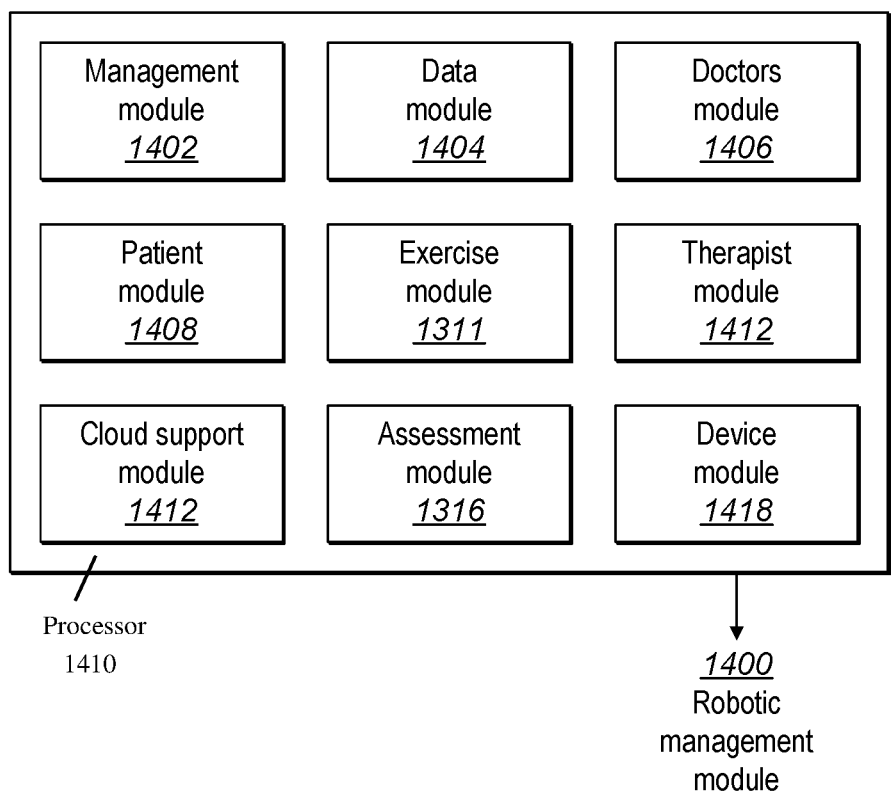
FIG. 14 shows a processor on a hardware/device/mobile device various modules.
Figure 15:
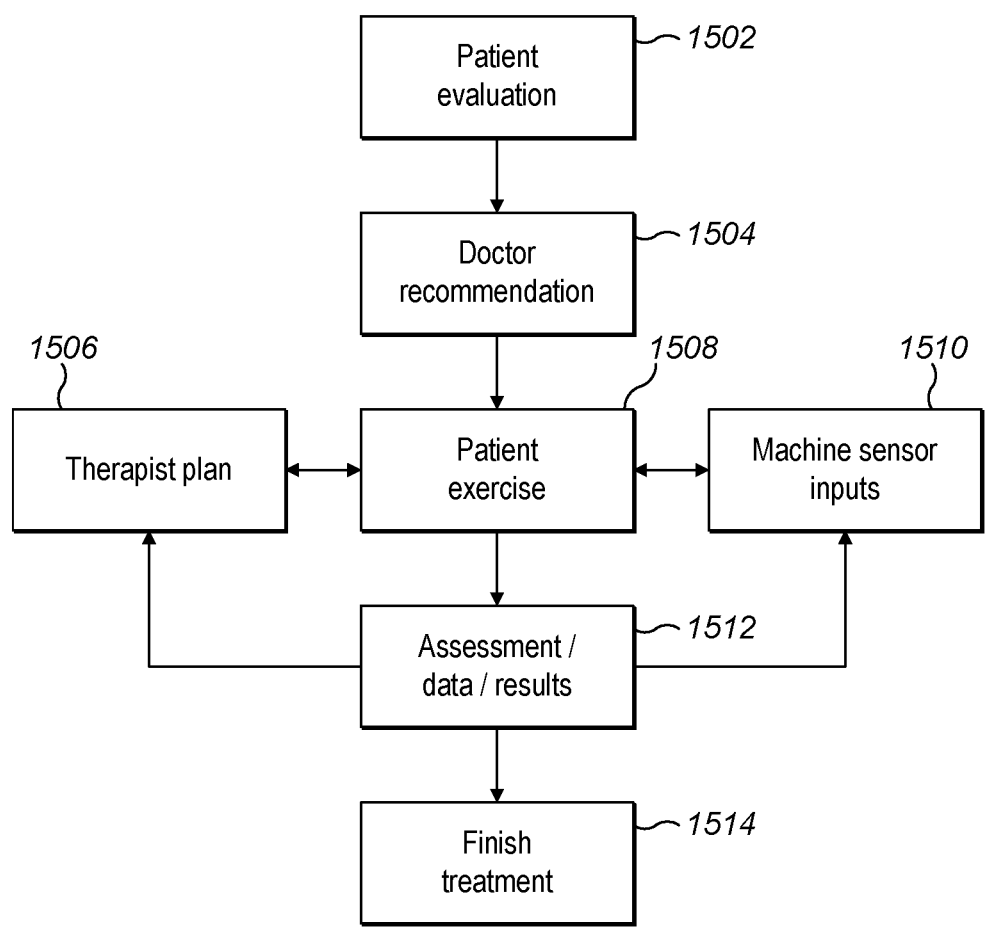
FIG. 15 shows a flow chart for the method of using the robotic limb rehabilitation apparatus and system.

FIG. 14 show that robotic management module 1400 is embedded in a processor 1410. It has many modules such as management module 1402, data module 1404, doctors module 1406, patient module 1408, exercise module 1311, therapist module 1412, cloud support module 1412, assessment module 1316 and device module 1418. This robotic management module 1400 is not just limited to these modules. More modules can be updated, uploaded and modified according to the need. Management module 1402 enables to do the patient evaluation 1502 if FIG. 15 to start a therapy session. The software is driven by the management module (1402) which setups the backend information about the hospitals/clinics, the users (doctors, therapists) and the patients. Based on the condition of the patient, the doctor can choose to enroll the patient for robotic rehabilitation. Using the doctor module (1406), the doctor now sets up a rehabilitation plan for the patient and uses one of the many rehabilitation measures using which they will measure the patient's progress. (The rehabilitation measure is a way of determining the state of the patient in a numerical assessment. As an example of the measure could be the SCI-FAP score which uses a set of 7 exercises and grades the patient on a scale of 2100 where lower the score, the better the patient is).

Once the doctor sets up the rehabilitation plan, the patient can now schedule sessions (1302) for the robotic rehabilitation with the therapist. The therapist now uses the Therapist module (1412) to define how many session and what exercises they would want to do in each session. They also define a session goal so that they can monitor the progress. The therapist has a bank of pre-defined exercises (1311) that they can use to plan the sessions for their patient. They can also create and add custom exercises if they want.

When the patient shows up for a session, the management module (1402) registers the same and this shows up in the therapist UI (1602). The therapist gets to know each of their patient and their conditions along with the assessment plan for them (1704). They calibrate the device (1802) to check that the device is functioning fine. Then they strap on the patient onto the device and run them through a BioFeedback (1910). This verifies that the device has been adjusted (1906) for the specific patient (adjusted to their height, hip-knee, knee-ankle lengths etc.). This also checks how the patient is feeling on this specific day (1908) (are they tired, do they have pain and so cannot stretch more today etc.). An object of the present invention is to provide a dynamic weight unloading mechanism wherein the therapist can control the amount of weight support to the patient/individual/user while being assisted by the exoskeleton. As a result, the patient/individual/user is exposed to controlled change in the body-weight balance which in turn promotes or teaches the patient/individual/user to self-balance.

The therapist now selects the protocols/exercises that they wish to administer to the patient (2002). This is based on the doctor's recommendations (1504) and the exercises that the therapist has setup. Going forward these recommendations will also be provided by the AI module which (1314) which uses machine learning algorithms to determine the best exercise for the patient's rehabilitation.

For any specific exercise the therapist can control the thresholds for the exercise (2102). For example: they can set the gait speed to a specific value. They can choose to reduce the stride length on a specific day as the patient might be complaining of pain when they stretch. However, the therapist could also choose the increase these thresholds—like leg lift if they feel that they pain/effort will benefit the patient's rehabilitation. According to an embodiment of the present invention, a transparent no resistance actuator control mode is utilized to address spasticity/movement i.e., in persons with locomotion disability covering therapeutic rehabilitation. According to an embodiment of the present invention, a system is provided for specific rehabilitative movements using reward/penalty mechanisms using Virtual Reality games specific to certain conditions such as Spinal Cord Injury (SCI), Stroke, etc.

According to an embodiment of the present invention, a smart system is provided to sense intent to turn (other than dual supports for body weight support). Depending on the patient's disease and patient exercise (1508) requirements, the Mobile-frame provides holistic gait training for the patient with better results, both in terms of faster attainment of outcomes as well as higher locomotive capabilities.

The robotic lower limb rehabilitation apparatus that combines the mechanism of both dynamic weight unloading system, mobile-frame and lower extremity exoskeleton device in conjunction with common power, controls and optimized actuators and motors using the machine sensor inputs 1510.

The user interaction force sensors sense if there are any abnormalities and in case if any abnormality is found then the system goes into transparent control mode on the lower extremity exoskeleton device and reducing the lower extremity exoskeleton device to ZERO resistance, and simultaneously the dynamic weight unloading mechanism goes into SAFE mode holding up the user's full weight. This allows the user's legs to shake freely without experiencing any high forces, and prevents falling. Further, this prevents the actuation motors from high torques and burnouts. The assessment module 1512 continuously not only records the exercise routine but also helps therapist plan 1506 and the machine sensor inputs to be corrected after the data is collected using this assessment module. Once the satisfactory results are achieved the treatment is finished for the day 1514.

The robotic lower limb rehabilitation system is provided to introduce intentional and controlled perturbations as a part of the rehabilitation. The combination of the dynamic weight unloading mechanism and lower extremity exoskeleton device allows such perturbation forces to be initiated without any safety concerns, enabling better and faster rehabilitation therapy. Furthermore, a Virtual Reality system is provided for immersing the user into a real-world situation, and by sensing the user's gait/forces appropriate actuation can be initiated for best therapy results. Also, the robotic lower limb rehabilitation has a sensing module which includes but not limited to one or more sensors, is capable to sense the user's intent to move forward, stop and turn.

In one scenario, the user is unable to perform any activity within a predefined limit such as walking or holding something as part of therapeutic rehabilitation. In such scenario, a control unit inbuilt in the robotic lower limb rehabilitation apparatus gets activated and provides necessary assistance in control manner to enable patient/user to perform such activity as assigned. The assistance in control manner is provided in such a way that the user is able to overcome such weakness slowly.

In one embodiment, the robotic lower limb rehabilitation apparatus is adapted to use specific rehabilitative movements using reward/penalty mechanisms such as in games. This is a non-traditional way to train and rehabilitate the patient. According to the embodiment, the robotic lower limb rehabilitation apparatus and system may include a virtual reality system (VR system) for providing training/therapy to the user/patient in which the system determines the level or capability of the user and assigns a task. The level of task is in such a way that the user can able to execute the same and also improves his/her motor ability. The user is awarded upon successfully completion of said task. Award system motivates the user to repeat the same again and again and simultaneously improves on his physical weakness. In case the user is unable to complete said task, the user is penalized. This award and penalty mechanism motivates the user to take additional effort to execute said task which in turn help him in overcoming the disability. Additionally, the VR system enables user/patient to train and execute the task correctly in the absence of therapist proper attention or caliber.

The robotic lower limb rehabilitation apparatus is operated/controlled using software that is principally of 4 types: Therapist UI from where the commands are given and progress is monitored, Controls software that has the configurations/settings for various parameters (torque, power etc.) for a certain disease state (e.g. SCI) and a specific patient—these would be robotic rehab protocols that are converted to software form, Application to record sensor data comprehensively and accurately and generate reports and artificial intelligence (AI) software to detect patterns in the data collected and thereby enable recovery predictions as well as efficacy of protocols.

The method of using the robotic lower limb rehabilitation apparatus is done as follows: the patient is brought to the mobile-frame in a wheelchair by a member of the hospital staff. The physiotherapist puts harness jacket on patient and clasps the hooks from BWS on jacket while the patient sits in the wheelchair. Donning/Doffing of the harness can be easily secured through straps made from human skin friendly material and locking mechanism. The physiotherapist presses button, which activates the dynamic body weight system (DBWS). The DBWS enables a powered winch to lift the patient to a semi-standing pose (with the appropriate unweighing). Unweighing means part of the patient is borne by the system thereby helping fragile patients.

Initially, a percentage of unweighing is set for a patient. However, due to the motion of the patient during setup, fluctuations in load are sensed by the system. The cylindrical load cell detects the resultant tension, which in turn is sent to the electronic controller. Using proprietary feedback control algorithm, instantaneous actuation signals are sent to the motors so that the patient feels a constant load relief. The physiotherapist then straps the lower extremity exoskeleton device onto the patient (easier to do since wheelchair does not hinder—there is 360 degrees access all around patient).

The lower extremity exoskeleton device can be easily mounted on to the patient with the help of adjustable skin friendly material clamps. The adjustable clamps would ensure that the lower extremity exoskeleton device addresses patients of varied populations, sizes and body shapes. This would also ensure that the less man power is required while strapping the Exo on the patient. The battery and the computer are not on the lower extremity exoskeleton device (they are on the DBWS) which makes the lower extremity exoskeleton device much lighter. The lower extremity exoskeleton device and the DBWS are connected through a connecting port with a tethered cable. This ensures supply of power and signals from the batteries and computers housed in the mobile frame to various motors and sensors on the lower extremity exoskeleton device. As the power source is away from the lower extremity exoskeleton device, the battery technology need not be complicated.

The physiotherapist presses the full stand mode which lifts the patient to a full stand mode. The person is now upright and hands free (No crutches are needed). The side arm bars are for the patient to feel secure but are not needed for locomotion. The patient starts walking slowly on the floor and the robotic lower limb rehabilitation apparatus follows. Locomotion on the floor is aided by two sets of wheels, one for steering and the other for driving the mobile-frame. In addition, multiple sensors like the rotary potentiometer are provided on the DBWS for sensing patient's intent to move or stop. The side arm bars are for the patient to feel secure but are not needed for weight bearing support. The side arm bars are provided with sensors which aid in providing turning inputs to the DBWS. The patient will not fall during the walk (in spite of there being no human support) owing to the harness. In case he loses balance, the patient will be "caught" by the harness with minimal jerk. When a patient fails to control voluntary movement, a smart control unit with multiple sensors detects the unusual movements and provides a signal to the controlling module. The controlling module processes the signals via proprietary algorithm and instantaneously transfers the system into appropriate transparent mode or fail safe mode in order to avoid any harm to the patient or Mobile-frame apparatus. Being an internet of things (IOT) device, locomotion parameters of the patient are captured automatically and stored. The robotic lower limb rehabilitation apparatus is portable within the hospital and can be wheeled easily to another room using the adjustable boom.

The robotic lower limb rehabilitation apparatus is suitable for more serious injuries and neuro-rehabilitation i.e. patient needs the lower extremity exoskeleton device to propel him/her forward and initiate walking while the harness helps to avoid fall. Note that the DBWS alone (excluding the lower extremity exoskeleton device) can be used for lesser injuries/advanced recovery i.e. patient has strength in legs to move forward but needs to learn balance and strengthen leg muscles for independent locomotion.

Rehabilitation is a customized process using artificial intelligence module for each patient—and also for each specific day. The software analyzes the entire background of the patient, the bio-feedback on a specific day and also the overall recommendation based on machine learning algorithm. It then uses this to drive the hardware: for example determining the power assist required at the left hip. Using the sensors, it can assess if the patient is putting more weight on one foot and if that has an impact on the muscle in that leg. Using this information, it can vary the power-assist allowing the patient to move that specific leg more easily.

Once the session is started, the system collects data from the various on-board sensors (2206, 1510) and also maps it onto the patient activity (2202). The detailed activities (2204) are logged and are also analyzed in real time for alerts (2504). This data that is collected is analyzed in the data module (1404) and stored in the database (1308). These assessment results (1512) are converted into reports which are available to all concerned parties including the patient, doctors, therapists and the insurance personnel.

All the data is stored in the cloud support module (1412) which is used for the AI learning (1314). This bank of data is what makes the system smart and allows the robotic device to be personalized and customized for each patient for each rehabilitation session.

Figure 16:
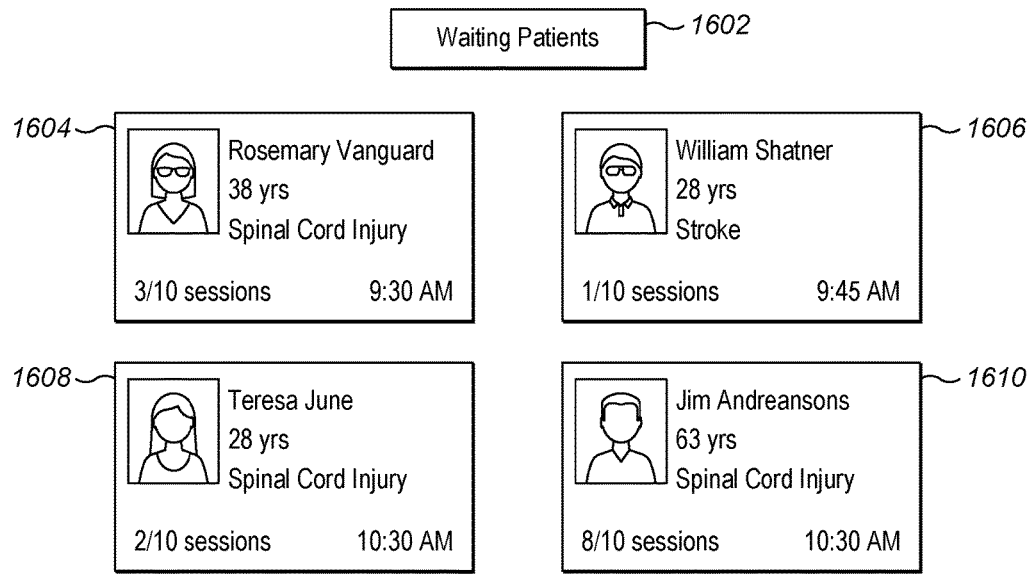
FIG. 16 shows a therapist graphical user interface on a mobile device.
Figure 17:
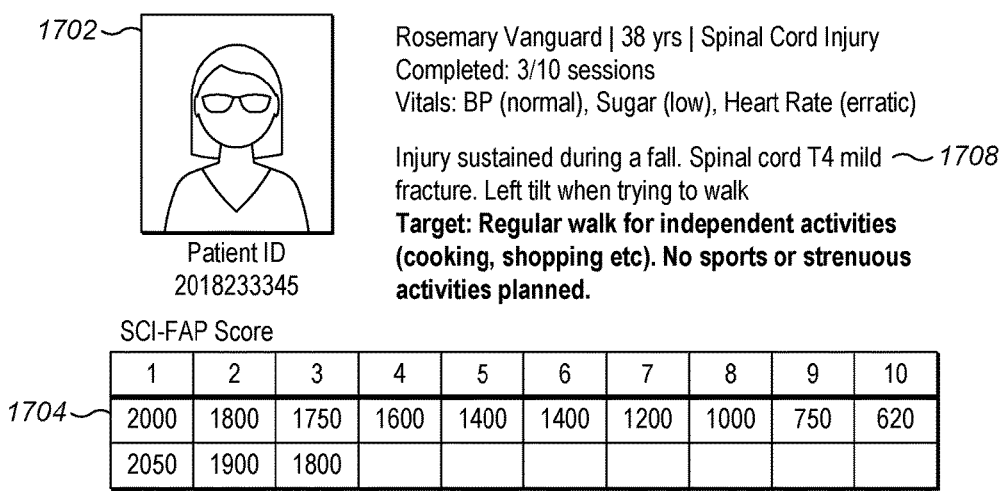
FIG. 17 shows a detailed therapist graphical user interface for one patient.
Figure 18:
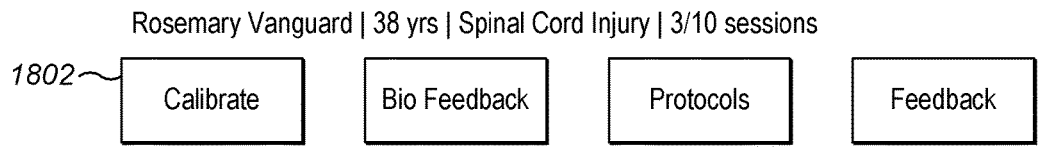
FIG. 18 shows starting of calibration for a patient in therapist interface.
Figure 18:
Figure 19:
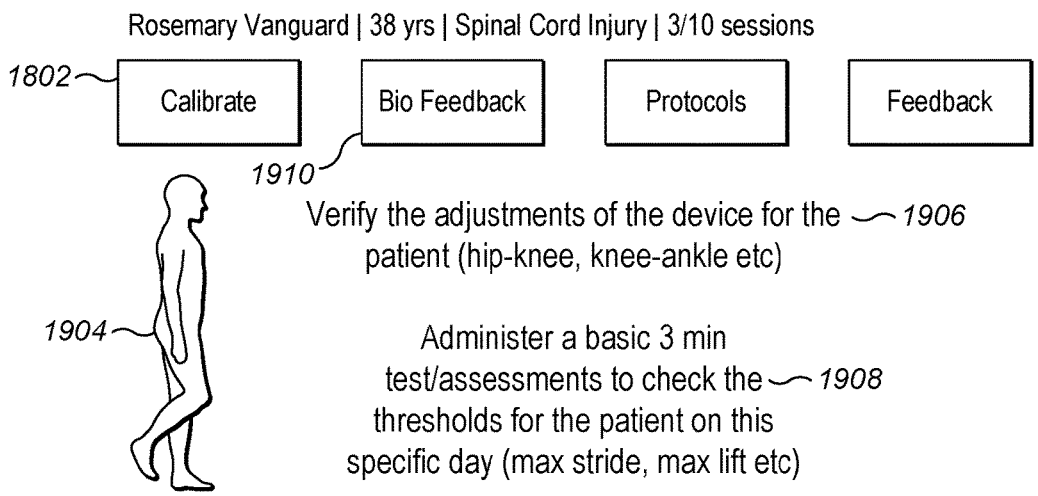
FIG. 19 shows Biofeedback for the exercise after calibration.
Figure 20:
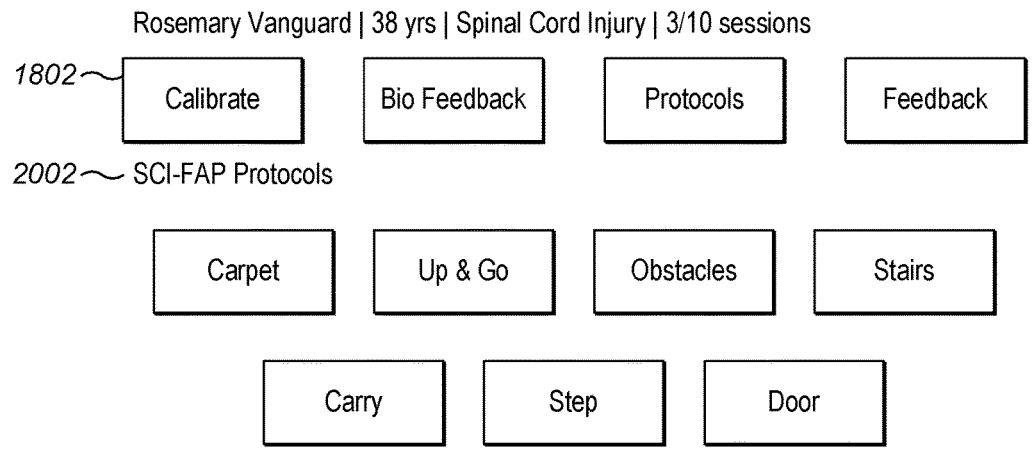
FIG. 20 shows the therapist using the protocols page for the patient.

FIG. 16 shows a graphical user interface for a therapist that has waiting patient list 1602, four patients 1604, 1606, 1608 and 1620 showing different season status. FIG. 17 shows for a patient 1702 the status, notes 1708 and spinal cord injury functional ambulation profile score (SCI-FAP score) after the start of the robotic rehab 1706. The user interface further shows many tabs in FIG. 18, FIG. 19 and FIG. 20 to show calibrate, bio feedback, protocols and feedback 1802 and items such as air walk 1804 data. FIG. 19 shows biofeed back 1910 for a patient 1904 and verify adjustments 1906 and administer test 1908. FIG. 20 offers Sci-fap protocols 2002.

Figure 21:
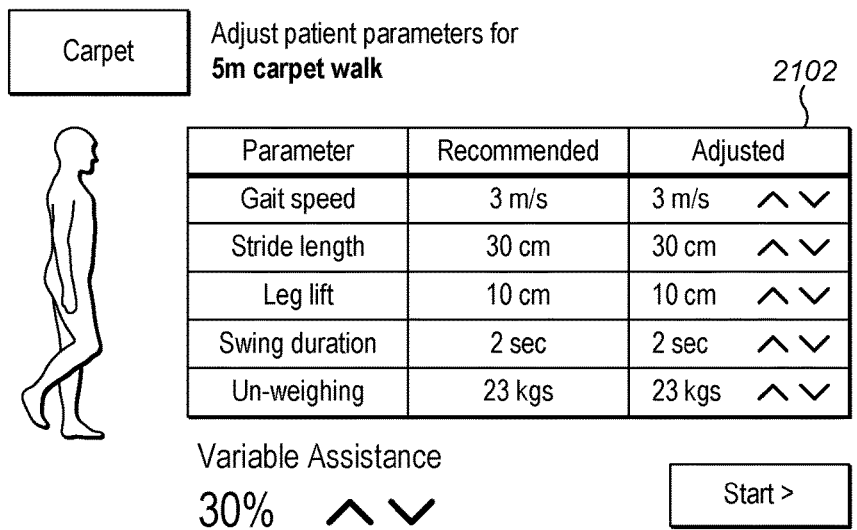
FIG. 21 shows the patient being tested for walking on a carpet.
Figure 22:
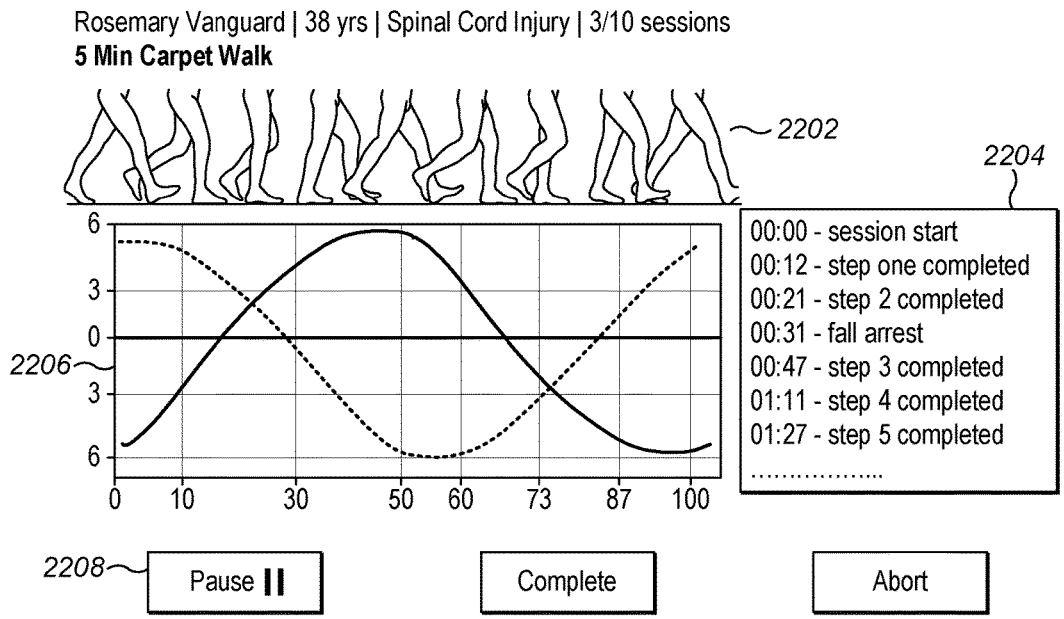
FIG. 22 shows the results of the patient walking on the carpet.
Figure 23:
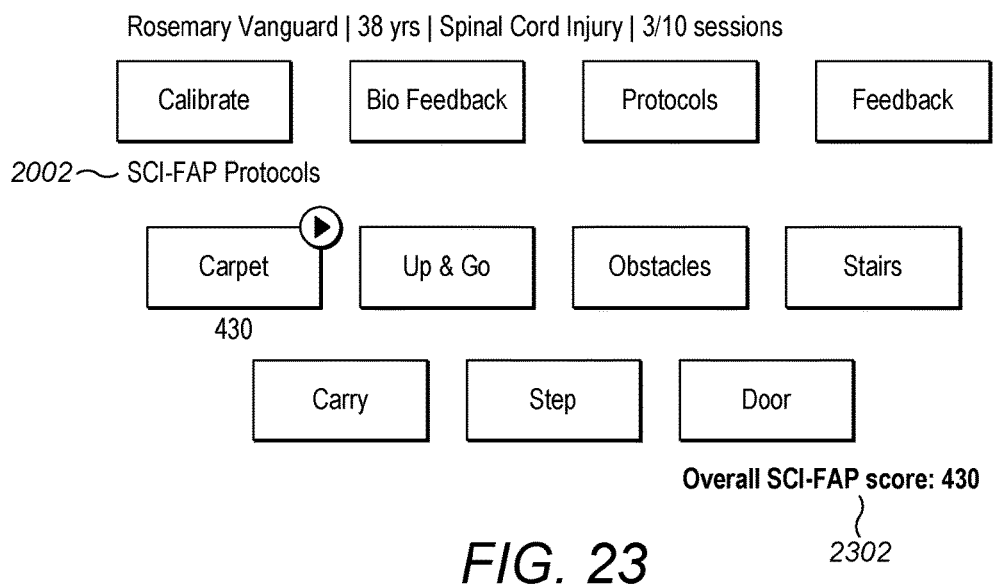
FIG. 23 shows subsequent steps for the patient on the rest of the protocol.
Figure 24:
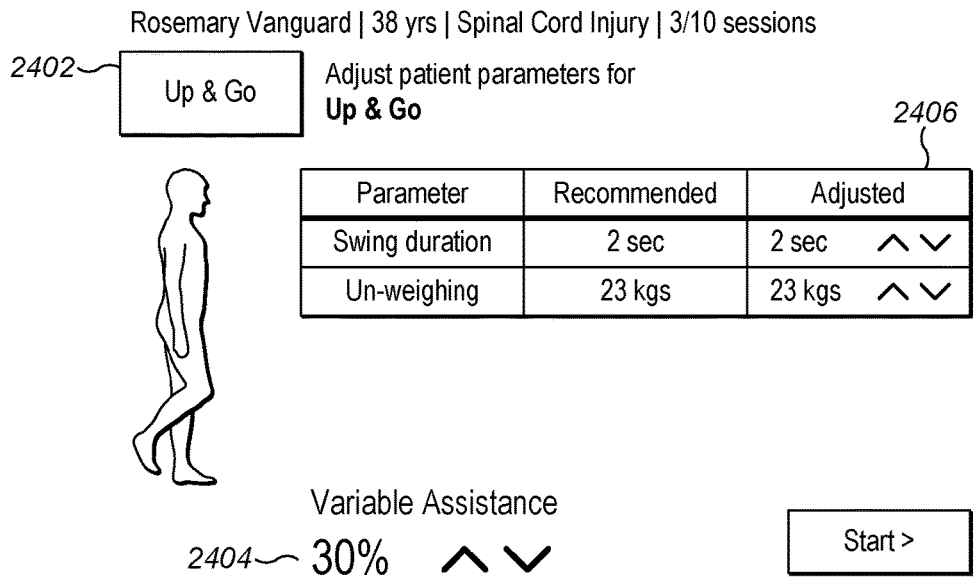
FIG. 24 shows results of the up and go test used for patient.
Figure 25:
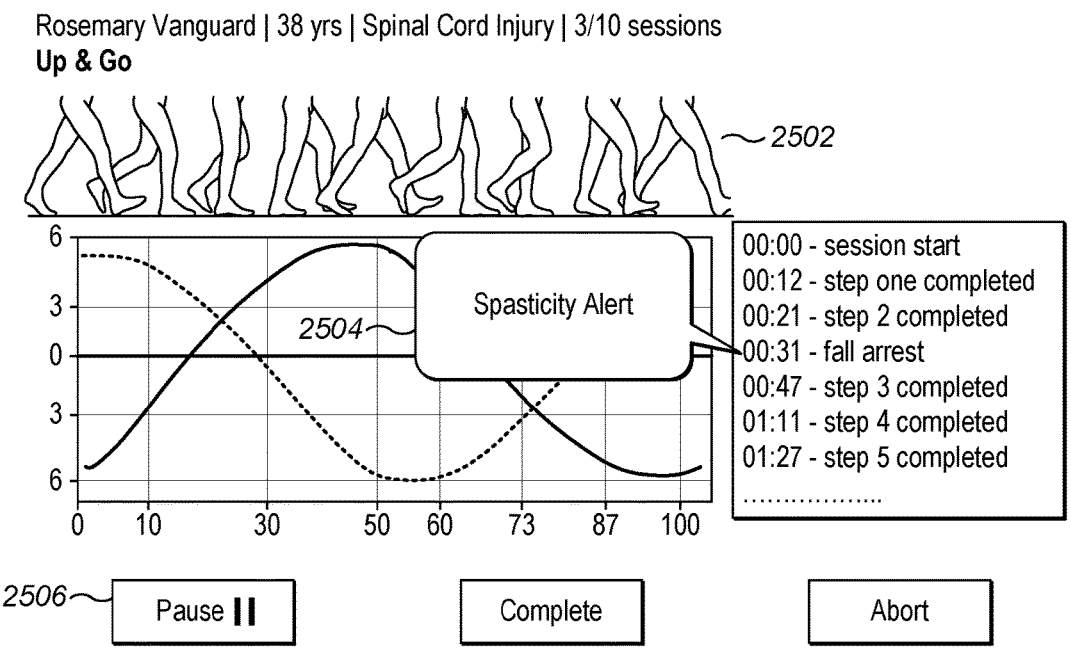
FIG. 25 shows if there are alerts for patients during exercise.
Figure 26:
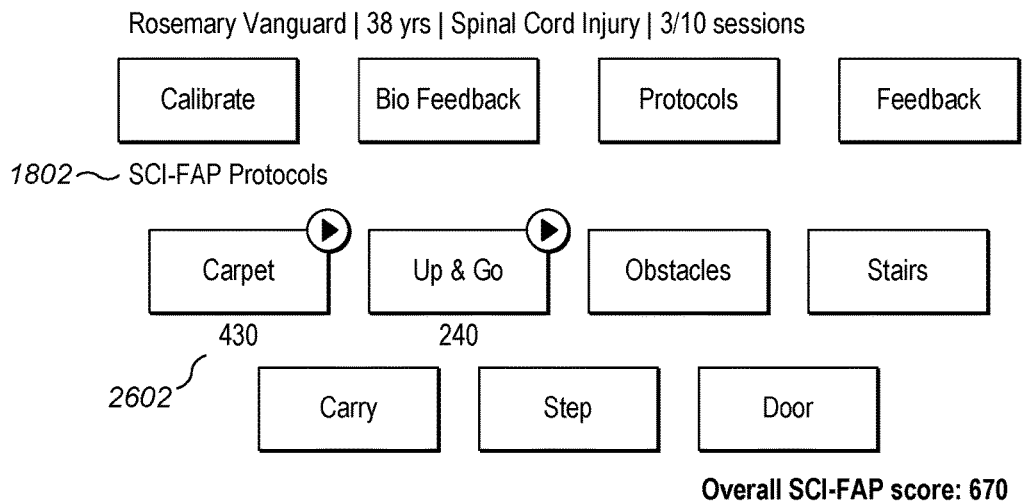
FIG. 26 shows the results of the tests that have been performed.
Figure 27:
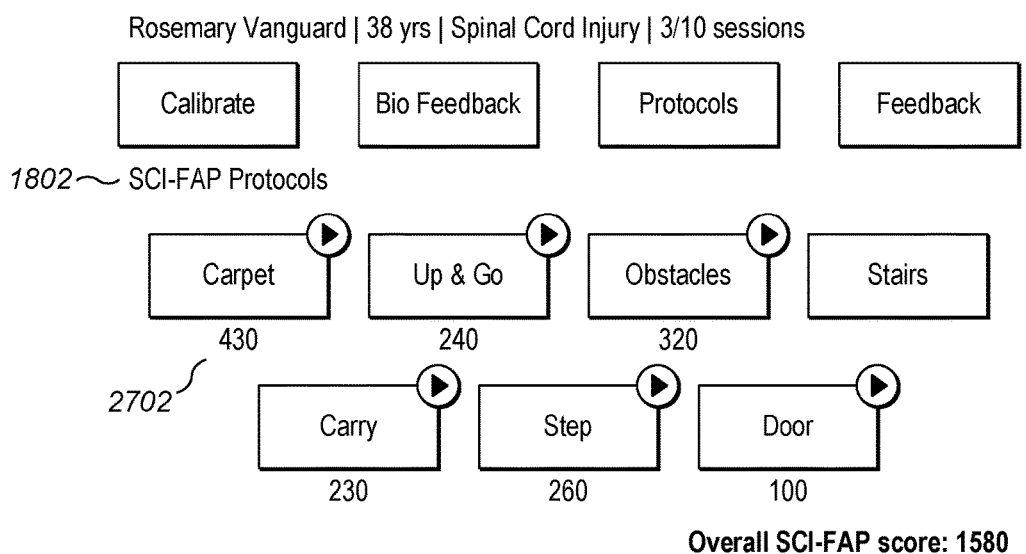
FIG. 27 shows a therapist dash board showing all the protocols being finished and their scores.
Figure 28:
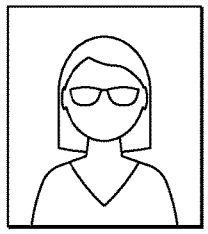
FIG. 28 shows the therapist dash board showing an entire set of finished results.

FIG. 21 shows adjusted parameters 2102. FIG. 22 shows gait 2202 on carpet, session completion 2204, and a pause button 2208. FIG. 23 shows overall score for the patient 2302. FIG. 24 further elaborates on adjusted scores 2406 and another exercise 2402 say up and go. The variable assistance is recorded as well at 2404. FIG. 25 shows how interactive this Mobile-frame apparatus is by recording spasticity alert 2504 for a gait 2502 and a therapist or patient can hit a pause button 2506. FIG. 286 shows various scores 2602 for the given patient. FIG. 27 sums up all other exercise assessment scores 2702 for a given SCI-Fap protocol for a specific patient. The doctor, therapist and patient can further review 2806 and see the scores 2804 and comments 2802 in FIG. 28.

Although the embodiments herein are described with various specific embodiments, it will be obvious for a person skilled in the art to practice the invention with modifications. However, all such modifications are deemed to be within the scope of the claims. It is also to be understood that the following claims are intended to cover all of the generic and specific features of the embodiments described herein and all the statements of the scope of the embodiments which as a matter of language might be said to fall there between.

What is claimed is:

1. A robotic limb rehabilitation apparatus, comprising:
   a mobile-frame having a first vertical support member and a second vertical support member connected by a horizontal cross bar carrying a boom arm assembly, wherein the boom arm assembly is configured to be vertical and while the patient walks slowly on the floor with the robotic rehabilitation apparatus following the patient;
   a wheel for each vertical supports for making the robotic limb rehabilitation apparatus mobile;
   a lower extremity exoskeleton device with multiple sensors for communicating an exercise parameter and its affect to a doctor, a therapist and the user in real time;
   a rope assembly (600) of the robotic limb rehabilitation apparatus comprises of a pulley 1 (612) on sliding carriage of a dynamic weight unloading mechanism, a pulley 2 (604) in the right vertical structural support member (122), a pulley 3 (606) housed in the horizontal cross bar (104), a pulley 4 (608) housed in the boom arm assembly (304), a flexible rope (602), a spreader bar (214) and a winch assembly (610 or 108);
   a therapist seat to assist the patient during a therapy session; and
   a robotic management module that controls the robotic limb rehabilitation apparatus during a therapy session by receiving input from the therapist, doctors and users.

2. The apparatus of claim 1, further comprising:
   the lower extremity exoskeleton device comprises of a waist band, a leg brace secured with two cuffs at a pair of locations for locking the waist band to a spread bar, a torso securing strap and a pelvis securing straps.

3. The apparatus of claim 1, wherein the first vertical support member of the mobile-frame comprises of a cylindrical load cell, a motor to control ball screw, a motor to control a winch drum, a coupling arrangement, a pair of springs, a pair of ultrasonic sensors and a string potentiometer.

4. The apparatus of claim 1, wherein the second vertical support comprises of a ball screw, a motor to control the ball screw, a ball nut, a coupling, a pulley, an ultrasonic sensor, a guide rails, an end support at upper and lower support plate, an upper spring support plate with the ball nut, and a lower spring support plate with a pulley.

5. The apparatus of claim 1, further comprising:
   a first motor to control a hip joint and a second motor to control a knee joint and a pair of shank clamps connects to a foot pad, and is not motorized, and is arranged to adjust as per the user's position.

6. The apparatus of claim 1, wherein the robotic management module comprises of a management module, data module, doctors module, patient module, exercise module, therapist module, cloud support module, assessment module and a device module to operate the robotic limb rehabilitation apparatus.

7. The apparatus of claim 6, wherein the robotic management module also includes session scheduling and reporting module and an artificial intelligence module to plan, evaluate, reassess and design exercise schedule for a user.

* * * * *